(12) United States Patent
Lindh, Sr. et al.

(10) Patent No.: US 9,206,535 B2
(45) Date of Patent: *Dec. 8, 2015

(54) SYSTEMS AND METHODS FOR MAKING BRAIDED BARBED SUTURES

(71) Applicant: Ethicon, Inc., Somerville, NJ (US)

(72) Inventors: David C. Lindh, Sr., Flemington, NJ (US); Jason T. Perkins, Bethlehem, PA (US); Krasimira Hristov, Belle Mead, PA (US); Jesse G. Nawrocki, Annandale, NJ (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,054

(22) Filed: May 23, 2014

(65) Prior Publication Data

US 2014/0290470 A1 Oct. 2, 2014

Related U.S. Application Data

(63) Continuation of application No. 13/463,883, filed on May 4, 2012, now Pat. No. 8,733,223, which is a continuation of application No. 12/548,984, filed on Aug. 27, 2009, now Pat. No. 8,210,085.

(51) Int. Cl.
*D04C 3/48* (2006.01)
*A61B 17/06* (2006.01)
*A61B 17/00* (2006.01)

(52) U.S. Cl.
CPC ............ *D04C 3/48* (2013.01); *A61B 17/06166* (2013.01); *A61B 2017/00526* (2013.01); *A61B 2017/06176* (2013.01)

(58) Field of Classification Search
CPC ........................ D04C 3/48; A61B 2017/06176
See application file for complete search history.

(56) References Cited

U.S. PATENT DOCUMENTS

| | | |
|---|---|---|
| 3,608,095 A | 9/1971 | Barry |
| 4,233,025 A | 11/1980 | Larson et al. |
| 4,510,934 A | 4/1985 | Batra |

(Continued)

FOREIGN PATENT DOCUMENTS

| | | |
|---|---|---|
| EP | 476306 | 3/1992 |
| WO | 2007120138 | 10/2007 |

(Continued)

OTHER PUBLICATIONS

Ethibond Excel Polyester Suture, http://ecatalog.ethicon.com/sutures-non-absorbable/view/ethibond-excel-suture, 14 pp. (2009).

*Primary Examiner* — Shaun R Hurley
(74) *Attorney, Agent, or Firm* — Doherty IP Law Group LLC

(57) ABSTRACT

A system for making braided barbed sutures includes a filament winding assembly, a barbed insert including an elongated core and barbs extending outwardly from the elongated core, and a barbed insert dispenser opening defining a passageway for orienting the barbed insert as the barbed insert is dispensed into the filament winding assembly. The barbed insert dispenser opening allows longitudinal movement of the barbed insert relative to the barbed insert dispenser opening while simultaneously preventing twisting movement of the barbed insert relative to the barbed insert dispenser opening.

20 Claims, 21 Drawing Sheets

(56) References Cited

U.S. PATENT DOCUMENTS

| | | |
|---|---|---|
| 4,517,759 A | 5/1985 | Wall |
| 4,519,290 A | 5/1985 | Inman et al. |
| 4,546,769 A | 10/1985 | Planck et al. |
| 4,549,545 A | 10/1985 | Levy |
| 4,620,473 A | 11/1986 | Bull |
| 4,803,909 A | 2/1989 | Smith |
| 5,217,495 A | 6/1993 | Kaplan |
| 5,341,758 A | 8/1994 | Strickland |
| 5,383,904 A | 1/1995 | Totakura |
| 5,593,424 A | 1/1997 | Northrup, III |
| 5,654,568 A | 8/1997 | Nakao |
| D400,937 S | 11/1998 | Lun |
| 5,931,855 A | 8/1999 | Buncke et al. |
| 6,066,160 A | 5/2000 | Colvin |
| 6,314,856 B1 | 11/2001 | Keith et al. |
| 6,475,229 B1 | 11/2002 | Pagedas |
| 6,506,197 B1 | 1/2003 | Rollero |
| 6,610,071 B1 | 8/2003 | Cohn |
| 6,776,789 B2 | 8/2004 | Bryant |
| 7,744,611 B2 | 6/2010 | Nguyen |
| 8,210,085 B2 | 7/2012 | Lindh et al. |
| 8,733,223 B2 | 5/2014 | Lindh et al. |
| 2003/0149447 A1 | 8/2003 | Morency |
| 2004/0060409 A1* | 4/2004 | Leung et al. ............... 83/522.14 |
| 2004/0106847 A1 | 6/2004 | Benderev |
| 2004/0226427 A1 | 11/2004 | Trull |
| 2006/0229675 A1 | 10/2006 | Novoa |
| 2007/0005110 A1 | 1/2007 | Collier et al. |
| 2007/0038249 A1 | 2/2007 | Kolster |
| 2007/0257395 A1 | 11/2007 | Lindh et al. |
| 2009/0099597 A1 | 4/2009 | Isse |
| 2009/0306710 A1 | 12/2009 | Lindh, Sr. |
| 2009/0312791 A1 | 12/2009 | Lindh, Sr. |
| 2010/0023055 A1 | 1/2010 | Rousseau |
| 2010/0160961 A1 | 6/2010 | Nawrocki |
| 2011/0251640 A1 | 10/2011 | Lauria |

FOREIGN PATENT DOCUMENTS

| | | |
|---|---|---|
| WO | 2009097556 | 8/2009 |
| WO | 2009129251 | 10/2009 |

* cited by examiner

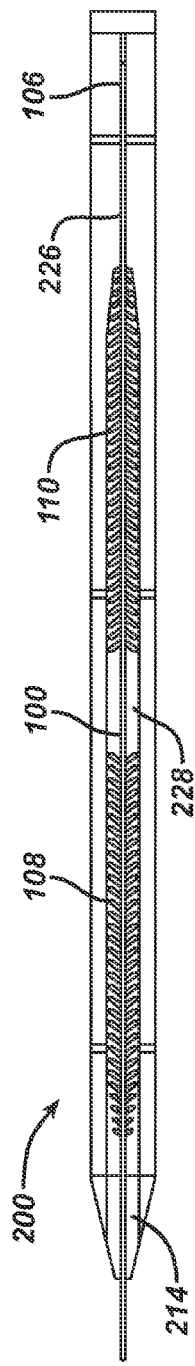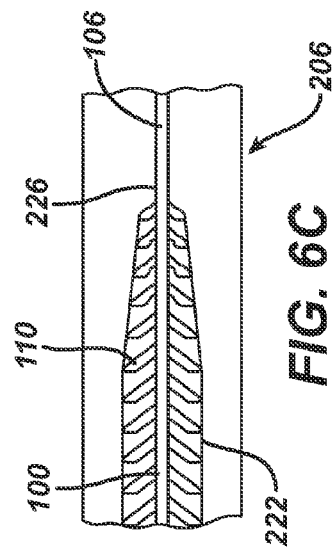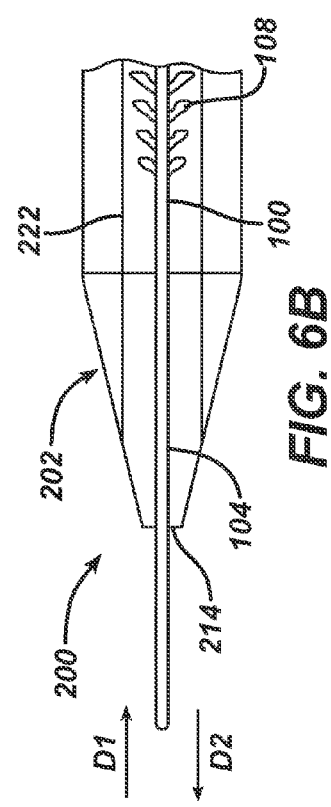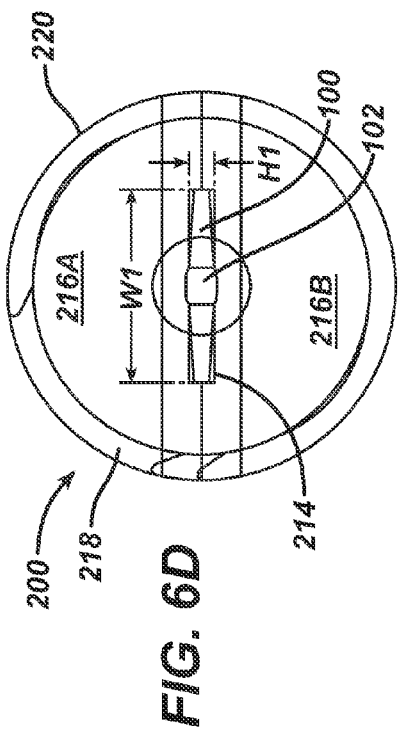

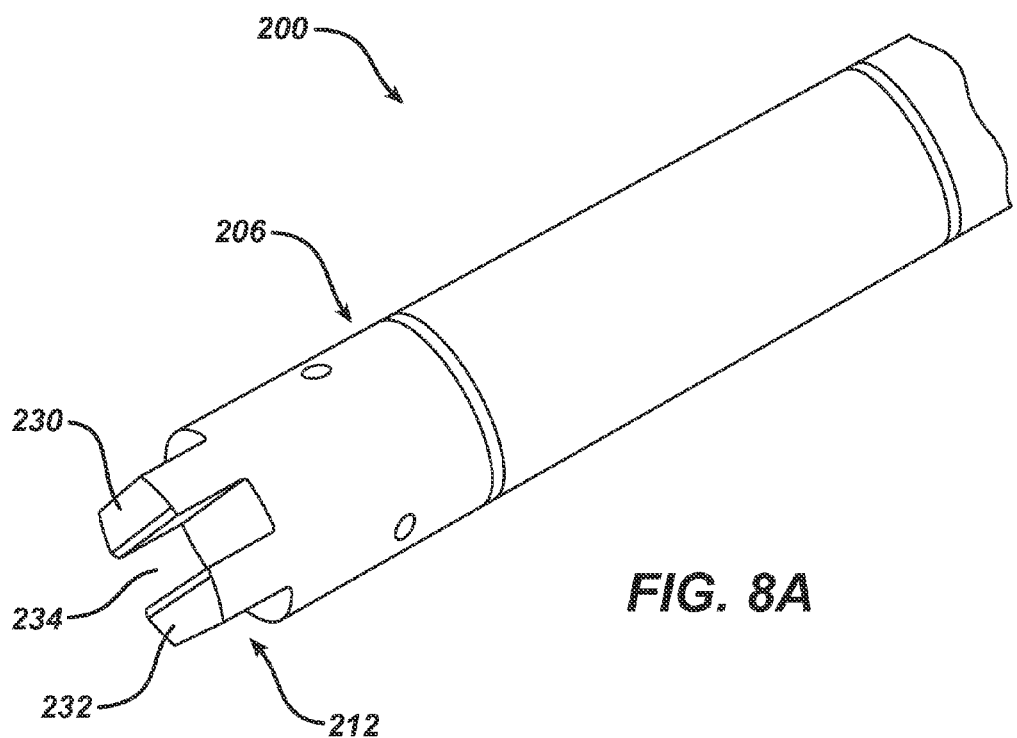

SYSTEMS AND METHODS FOR MAKING BRAIDED BARBED SUTURES

CROSS REFERENCE TO RELATED APPLICATIONS

The present application is a continuation of U.S. patent application Ser. No. 13/463,883, now U.S. Pat. No. 8,733,223, which is a continuation of U.S. patent application Ser. No. 12/548,984, now U.S. Pat. No. 8,210,085, which is related to commonly assigned U.S. patent application Ser. No. 12/549,046, now U.S. Pat. No. 9,011,487, the disclosures of which are hereby incorporated by reference herein.

BACKGROUND OF THE INVENTION

1. Field of the Invention

The present invention generally relates to surgical sutures, and more specifically relates to automated systems and methods for making braided barbed sutures.

2. Description of the Related Art

Surgical sutures are used to close wounds and surgical incisions, and to repair damaged muscles, vessels, and tissue. Typically, a needle is attached to one end of a surgical suture, and the needle is drawn through tissue to form one or more loops holding the tissue together. The suture is subsequently tied off in one or more knots so that the tissue will remain drawn together.

There have been a number of attempts directed to improving sutures. For example, U.S. Pat. No. 4,546,769 to Planck et al. discloses a suture including a jacket made of a tubular braided structure, such as non-crimped yarns, and a core located within the jacket containing crimped fibers. The jacket is formed by braiding the non-crimped yarns around the core, which provides a suture that is easier to bend, easier to handle, and that makes better knots.

Although sutures are very effective for closing wounds, there are a number of challenges associated with using conventional sutures. Many of these challenges are directly related to the knots used to secure sutures in place. If the knots are not tied properly, defects may arise including slippage, knot breakage, and re-opening of the wound. In addition, using knots to secure sutures may distort tissue, restrict blood flow, increase the formation of scars, impede wound healing, and result in infection.

In response to the above-noted deficiencies associated with conventional sutures, sutures having barbs have been developed. Unlike conventional sutures, barbed sutures have projecting barbs that allow the suture to be used to close wounds, approximate tissue, tighten tissue, and attach prosthetic devices without using knots. U.S. Pat. No. 5,931,855 discloses barbed sutures that are used for cosmetic procedures such as brow-lifts and face-lifts. Fixing conventional sutures with knots requires the knots to be pushed down toward the tissue to assure proper tensioning and fixation of the sutures. In contrast, barbed sutures achieve proper tensioning and fixation by applying tension to the suture.

One problem associated with barbed sutures is that the barbs may delaminate or separate from the core of the suture, which may lead to device failure. In response to problems encountered with barbed sutures, braided barbed sutures having more durable barbs have been developed. In one embodiment of commonly assigned U.S. Patent Application Publication No. 2007/0005110, the disclosure of which is hereby incorporated by reference herein, at least one barbed filamentary element is intertwined along its length with a plurality of unbarbed filamentary elements, and the plurality of barbs extend outwardly beyond the unbarbed filamentary elements. In one embodiment, a braided barbed suture made using the methods disclosed in the '110 publication had a 96% improvement in holding strength compared to a barbed monofilament. Thus, superior holding strength was achieved without requiring the use of knots.

Other efforts for making braided, barbed sutures include manually delivering a barbed filament into a winding filament assembly. This approach requires an operator to adhere to a complex series of steps including running a braider to form a first length of unbarbed suture, turning the braider off, positioning a barbed filament at the braider eyelet where the filaments wind together, then turning the braider back on and allowing the winding filaments to draw the barbed filament into the braid. This approach provides very little control over the twisting of the barbed filament as it is drawn into the braid, which often results in undesirable braiding quality. This approach is also extremely labor intensive because an operator is required to continually turn the braiding equipment on and off while adjusting the position of the barbed filament. In addition, the barbed insert material being braided is greatly affected by the winding filaments themselves or by the vibration created as a result of winding. The vibration generated by the braiding equipment can result in the barbed material whipping, twisting, getting caught in the filaments, or accumulating undesirable rotation.

In spite of the above advances, there remains a need for improved systems and methods for making braided, barbed sutures, including automated systems and methods for making braided, barbed sutures. There also remains a need for improved systems and methods that consistently produce braided barbed sutures meeting exacting standards, and that transform barbed inserts having barbs in a single plane into braided barbed sutures having barbs in multiple planes.

SUMMARY OF THE INVENTION

In one embodiment, a system for making braided barbed sutures includes a filament winding assembly adapted to wind a plurality of filaments around an object, such as a barbed insert, and a guide assembly including at least one barbed insert dispenser opening defining a passageway for orienting a barbed insert. In one embodiment, the passageway is an elongated slit having a greater width than height. The guide assembly is preferably adapted to dispense at least one barbed insert from the dispenser opening and into the filament winding assembly so that the plurality of filaments may be wound about the barbed insert. The passageway of the dispenser opening is preferably adapted to allow longitudinal movement of the at least one barbed insert relative to the passageway while simultaneously prevented twisting movement of the at least one barbed insert relative to the passageway. In other words, the passageway is sized and shaped to enable the barbed insert to move freely along its longitudinal axis relative to the passageway. However, the passageway has a size and shape that substantially conforms to the size and shape of the barbed insert so that the barbed insert is constrained from rotating about its longitudinal axis relative to the passageway when the barbed insert is passing through the passageway.

Although the present invention is not limited by any particular theory of operation, it is believed that providing a passageway, such as an elongated slit, for dispensing a barbed insert provides enhanced control over the orientation and configuration of the barbed insert as it is introduced into the filament winding assembly. During a braiding operation, a barbed insert may twist, loop and/or rotate uncontrollably about its longitudinal axis as it is introduced into the filament winding assembly, which may result in the formation of braided barbed sutures having inconsistent quality. The present invention seeks to reduce the number of uncontrollable variables found in conventional braiding systems by more directly controlling the orientation and configuration of the barbed insert as it is introduced into the filament winding assembly. The present invention also provides an automated system that does not require continuous human oversight.

In one embodiment, a barbed insert includes an elongated core having a leading end, a trailing end, and a longitudinal axis extending between the leading and trailing ends thereof. The barbed insert preferably includes at least one barb, and preferably a plurality of barbs extending outwardly from the core. In one embodiment, the plurality of barbs includes a first set of barbs extending in a first direction, and a second set of barbs extending in an opposite second direction. In one embodiment, at least one set of barbs may taper outwardly between a first end and a second end, which preferably facilitates passage of the barbed suture through tissue.

In one embodiment, the passageway of the barbed insert dispenser opening desirably controls and/or prevents rotation of a barbed insert relative to the passageway when the barbed insert is in contact with the passageway and as the barbed insert is introduced into the filament winding assembly. In one embodiment, the barbed insert dispenser opening may be rotated as the barbed insert is dispensed therefrom for imparting rotation to the section of the barbed insert in contact with the passageway. Thus, although the barbed insert will not rotate about its longitudinal axis relative to the passageway, the barbed insert may be rotated by the passageway to provide a twist to the barbed insert. In one embodiment, the passageway is rotated as the barbed insert is dispensed so that the filaments are helically wound about the barbed insert, which, in turn, may result in transforming a barbed insert having barbs in a single plane into a braided barbed suture having barbs projecting in multiple planes, such as approximately 360° around the perimeter of the core.

The system described herein is preferably automated so that braided barbed sutures having consistent characteristics and quality may be produced. In one embodiment, the system preferably includes a system controller having a central processing unit for controlling operation of the system. In one embodiment, the system controller controls operation of the filament winding assembly and the guide assembly. The system controller may have a first state in which the dispenser opening is stationary as a barbed insert is dispensed into the filament winding assembly. The system controller may have a second state in which the dispenser opening is rotated as the barbed insert is dispensed into the filament winding assembly for providing a twist to the barbed insert as filaments are wound around the core of the barbed insert.

In one embodiment, a plurality of barbed inserts having finite lengths are introduced in series into the filament winding assembly. In this embodiment, the guide assembly preferably comprises a plurality of cartridges, each of the cartridges including one of the dispenser openings defining a passageway (e.g. an elongate slit) for orienting one of the barbed inserts. Each of the barbed inserts is preferably loaded into one of the cartridges so that a leading end of each barbed insert projects from the passageway of the barbed insert dispenser opening associated therewith.

In one embodiment, the guide assembly also includes a magazine for holding the cartridges and the system controller includes a subroutine for introducing the cartridges one at a time into the filament winding assembly. In one embodiment, a first loaded cartridge is introduced into the filament winding assembly so that the barbed insert loaded therein may be drawn into the filament winding assembly for producing a first braided barbed suture. After the barbed insert has been drawn from the first cartridge, the cartridge may be automatically removed from the system. A second cartridge including a barbed insert loaded therein may then be advanced into alignment with the filament winding assembly so that the second barbed insert in the second cartridge may be drawn into the braid for forming a second braided barbed suture. The second empty cartridge is then dispensed, and the process is repeated for delivering a series of loaded cartridges to the filament winding assembly and removing empty cartridges from the system.

In one embodiment, each of the cartridges preferably includes an optical window for providing visual access to the barbed inserts loaded therein. The system controller preferably includes an optical sensor and/or optical equipment for determining whether barbed inserts are present in the cartridges. In one embodiment, after a barbed insert has been drawn from a cartridge, the optical sensor determines that the barbed insert has been removed and that the cartridge is empty. At this point, the optical sensor transmits a signal to the system controller, which, in turn, generates one or more signals for removing the empty cartridge from the system and advancing the next loaded cartridge into alignment with the filament winding assembly.

In one embodiment, each cartridge includes an outer surface and the guide assembly preferably includes a cartridge insertion rod that engages the outer surfaces of the respective cartridges for controlling movement of the cartridges. In one embodiment, each cartridge includes a lower end that is keyed and the cartridge insertion rod includes an upper end that is keyed for meshing with the keyed lower end of the cartridge. In one embodiment, the opposing keyed ends enable the cartridge insertion rod to hold the cartridge from rotating about its longitudinal axis as the barbed insert loaded therein is drawn into the filament winding assembly. In one embodiment, the cartridge insertion rod may rotate under the command of the system controller for rotating the cartridge and the dispenser opening associated with the cartridge, which, in turn, provides a twist to the barbed insert as the insert is drawn from the dispenser opening of the cartridge.

In one embodiment, a system for making braided barbed sutures includes a filament winding assembly having a plurality of filaments, and a guide assembly for guiding at least one barbed insert toward the filament winding assembly. The guide assembly desirably has a barbed insert dispenser opening, such as an elongated slit, adapted to enable longitudinal movement of the barbed insert through the barbed insert dispenser opening while simultaneously preventing twisting movement of the at least one barbed insert relative to the barbed insert dispenser opening. In one embodiment, the filament winding assembly desirably includes a braider eyelet for directing the plurality of filaments toward a braiding zone. The guide assembly is adapted to direct a leading end of at least one barbed insert into the braiding zone for winding the plurality of filaments around the at least one barbed insert for making a braided barbed suture.

In one embodiment, at least one barbed insert has a longitudinal axis, and the barbed insert dispenser opening is rotatable as the barbed insert is dispensed from the barbed insert dispenser opening for rotating the barbed insert about its longitudinal axis as the plurality of filaments are winding around the barbed insert.

In one embodiment, a method of making braided barbed sutures includes providing a filament winding assembly having a plurality of filaments, and providing at least one barbed insert for introduction into the filament winding assembly.

The method preferably includes providing a barbed insert dispenser opening adjacent the filament winding assembly for dispensing the at least one barbed insert into the filament winding assembly. The barbed insert dispenser opening is preferably adapted to allow longitudinal movement of the at least one barbed insert relative to the barbed insert dispenser opening while simultaneously preventing twisting movement of the at least one barbed insert relative to the barbed insert dispenser opening. The method desirably includes dispensing the at least one barbed insert from the barbed insert dispensing opening and into the filament winding assembly. A plurality of filaments is preferably wound around the barbed insert as the barbed insert is dispensed from the barbed insert dispenser opening.

In one embodiment, the at least one barbed insert includes a core and at least one barb projecting outwardly from the core. In one embodiment, the barbed insert dispenser opening preferably defines an elongated slit having a size and a shape that substantially conforms to the size and shape of the at least one barbed insert. In one embodiment, when dispensing the at least one barbed insert, the barbed insert dispenser opening is preferably rotated for twisting the at least one barbed insert as the plurality of filaments are winding around the at least one barbed insert. This particular embodiment preferably transforms a barbed insert having barbs that lie in a single plane into a braided barbed suture having barbs projecting 360° around the perimeter of the core.

In one embodiment of the present invention, systems and methods are adapted to consistently incorporate insert materials into a multi-filament suture during braiding, which yields resultant device designs having inserts that are fully contained within the multi-filament braid, or resultant device designs having protrusions that extend out from the multi-filament braid in a single plane or in multiple planes. In one embodiment, barbed inserts of various sizes, shapes, materials or variations thereof may be incorporated into multi-filament sutures of various sizes and materials, including absorbable and non-absorbable materials. Novel braiding technologies such as those described herein provide a wide range of next generation suture-based devices. In one embodiment, the present invention provides for the fabrication of braided barbed devices in a full-scale manufacturing setting with consistent and repeatable results. The fully-automated features of the present invention eliminate the labor intensive aspect of delivering each barbed insert into the braid by hand.

In one embodiment, an individual barbed insert, having a finite distinct length, is placed into a cartridge and fed into a filament winding assembly during braiding. The result is a suture-based device having finite sections of braided barbed suture interposed between finite lengths of braided suture. In another embodiment, a continuous length of suture material having a barbed profile, like that of the individual barbed inserts, may be continuously fed from a spool through a guide and subsequently incorporated into the winding filaments during braiding, which provides a suture-based device comprised of a continuous length of braided barbed suture.

In one embodiment, the automated braiding equipment provides for braiding the winding filaments around a barbed insert with the desired protrusion of the barbs from the multi-filament suture. The automated braiding equipment enables a method of manufacture that consistently produces satisfactory braiding quality while significantly reducing the labor involved to achieve such devices. In one embodiment, a system operator may fill a magazine with loaded cartridges, program the desired braiding cycle parameters, and allow the automated braiding equipment to perform the braiding operation. Or, in the case of a continuous length of suture material having a barbed profile, the person operating the system may thread the lead end of a spool of barbed material through the guide and allow the suture filaments to wind around the barbed material until the barbed material runs out.

In one embodiment, the present invention also enables the manufacture of barbed suture devices with helically-shaped cores. The novel aspect of this resultant design is that the helical shape of the core can be controlled using the automated braiding equipment to create a fixation device that provides holding strength in 360° around the core.

In one embodiment, a magazine loaded with a plurality of cartridges is locked in place beneath a braider using a magazine tool. The braider is then turned on and a PLC-controlled cycle commences for delivering barbed inserts from the cartridges into the braid. At an appropriate time, a retractable gate is retracted and an air cylinder pushes the stack of cartridges toward the chamber for loading a lead cartridge in the chamber. The retractable gate then closes, isolating the loaded, lead cartridge in the chamber. A two-stage lift sequence may be initiated. During a first stage, an uplift rack with motor travels upward then stops. During a second stage, the uplift sequence allows a push rod to engage the bottom of the lead cartridge and initiate the upward travel of the rod and cartridge.

In one embodiment, as the cartridge approaches its maximum travel toward the winding filaments, but before the cartridge comes to a complete stop, the barbed insert is drawn out of the cartridge by the winding filaments. A fiber optic sensor detects when the barbed insert has been drawn out of the cartridge at which time the empty cartridge begins its downward travel. When the empty cartridge returns to the cartridge chamber, it is ejected and carried to a collection area via a cartridge ejection tube.

In one embodiment, a continuous length of suture material having a barbed profile is delivered through a guide and into a winding filaments assembly. The guide is adapted to deliver the barbed material to the winding filaments assembly. The lead end of the continuous length of barbed suture material is threaded through the guide and incorporated into the winding suture filaments. In one embodiment, the guide may be rotated as the continuous length of suture material is fed into the guide so that the resultant braided barbed suture will have a helical shape that is set by the braid itself. The present invention allows for braided barbed sutures having barbs or other protrusions present in a single plane or in multiple planes including a 360° helical design.

In one embodiment, a system for making braided barbed sutures includes a bullet-like cartridge adapted to receive barbed inserts having a finite length. In this embodiment, the cartridge is adapted to act as a vehicle for the delivery of a barbed insert into a braided multi-filament suture. The bullet-like cartridge includes a keyed slot at the bottom of the cartridge that prevents undesirable twisting motion of the barbed insert to enable braiding. The cartridge is affixed, and does not allow for the free movement of the insert as it is incorporated into the braid.

In one embodiment, the braider system includes a controller having timers, sensors, and cartridge deliver apparatus. The above-described controller is preferably combined with conventional braiding technology whereby the timers and sensors allow for a fully-automated, repeatable braiding cycle that enables the consistent formation of braided, barbed sutures. The cartridge deliver apparatus preferably allows for the physical delivery of the cartridge, which contains a barbed insert, to the suture filaments at desired suture length intervals. As the cartridge approaches its maximum travel toward the winding filaments, but before the cartridge comes to a complete stop, the barbed insert is desirably drawn out of the cartridge by the winding filaments themselves.

In one embodiment, the control system provides for control over variable motion/rotation, braiding speed, and cartridge delivery speed. In one embodiment, controlled rotation of the barbed insert during delivery into the suture filaments allows for a helical resultant device whereby the suture braid sets the twist of the core of the barbed insert via cartridge rotation.

In one embodiment, the braider system includes a cartridge magazine with retractable gate and ejection tube. The cartridge magazine with retractable gate and ejection tube preferably allows for a side-loading and bottom ejecting apparatus that enables delivery of a loaded cartridge into the suture filaments for braiding and the ejection of an empty cartridge after the barbed insert has been delivered into the braid.

In one embodiment, a braider system produces braided barbed sutures having a helical-shaped core with barbs protruding 360° around the core. The helical design preferably allows for barbs to engage 360° around the core rather than in a single plane. The 360° positioning of the barbs preferably increases the holding strength of the resultant device. The braider system of the present invention preferably enables an operator to transform a flat, barbed insert having barbs in a single plane into a multi-plane device. To date, such multi-plane devices were only achievable via methods such as cutting into monofilament sutures and twisting the resultant device or via injection molding.

In one embodiment, a braider system includes a rotatable guide for barbed inserts that accommodates a continuous length of suture material having a barbed profile, whereby the continuous length of suture material is fed from a spool and incorporated into a braid. In one embodiment, a continuous length of suture material having a barbed profile may be fed through the rotatable guide, incorporated into the braid, and collected on a collection spool. The guide is desirably attached to the equipment by an appropriate substructure. The guide is preferably rotatable as the continuous barbed material is fed through it to create a periodic helical design of the resultant device whereby the suture filaments set the orientation of the continuous length of barbed suture material.

These and other preferred embodiments of the present invention will be described in more detail below.

BRIEF DESCRIPTION OF THE DRAWING

FIG. 6A shows the barbed insert of FIG. 2 loaded in the cartridge shown in FIGS. 5A-5C.

FIG. 6B shows a leading end of the cartridge shown in FIG. 6A.

FIG. 6C shows a trailing end of the cartridge shown in FIG. 6A.

FIG. 6D shows a cross-sectional view of the cartridge shown in FIG. 6A.

FIG. 8A shows a perspective view of a lower end of the cartridge of FIG. 3, in accordance with one embodiment of the present invention.

DETAILED DESCRIPTION

Figure 1:
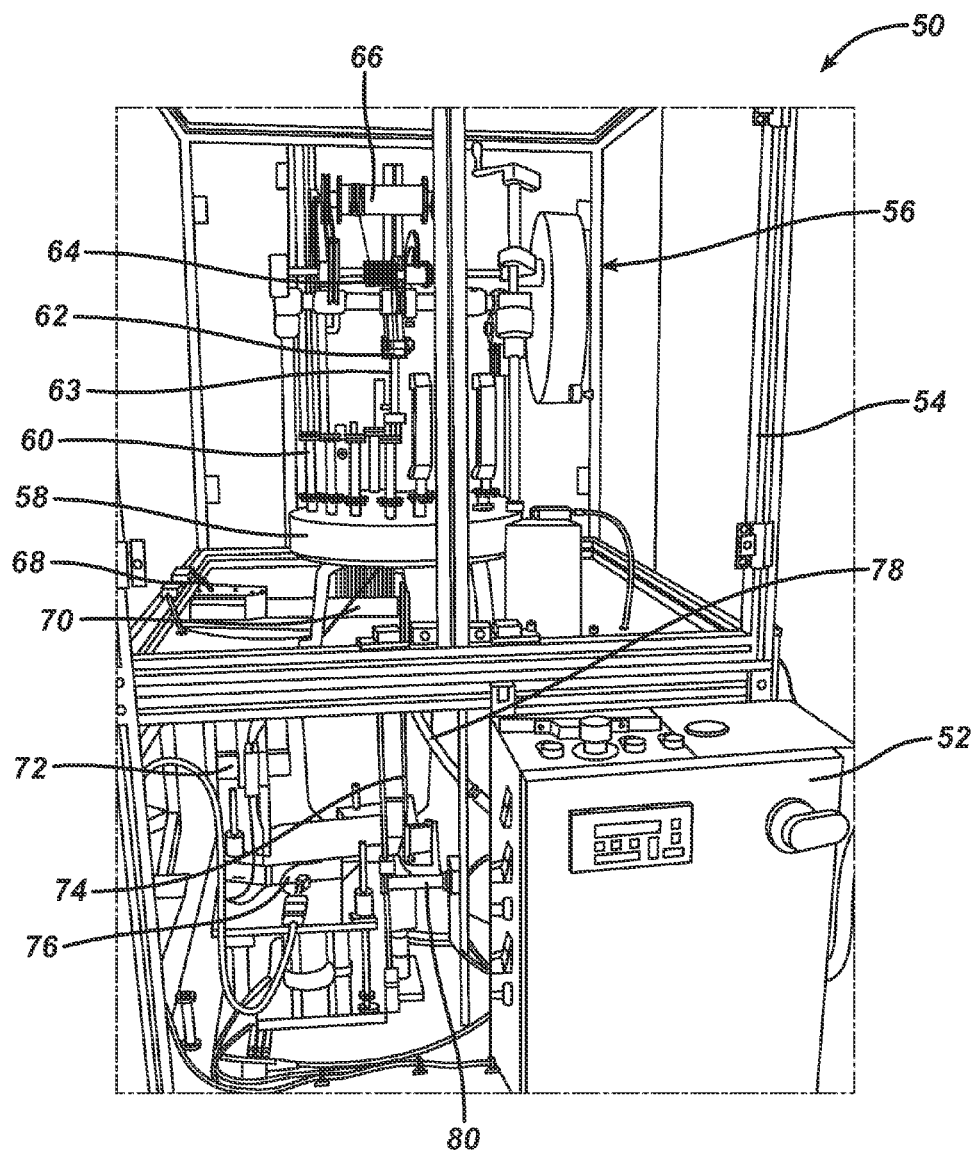
FIG. 1 shows an automated system for making braided barbed sutures, in accordance with one embodiment of the present invention.

Referring to FIG. 1, in one embodiment of the present invention, an automated system 50 for making braided barbed sutures includes a system controller 52 for controlling operation of the system. The automated system 50 preferably includes an enclosed area 54 that houses a braider assembly 56 adapted for winding filaments around barbed inserts to form braided barbed sutures, as will be described in more detail below. The braider assembly 56 preferably includes a braider plate 58 and bobbins 60 that contain multi-filaments that are positioned around the braider plate 58. The braider assembly 56 desirably includes a braider eyelet 62 for directing the filaments toward a central braiding zone, a cartridge guide tube 63, a braider dowel 64 and a suture collection spool 66. The braider system also preferably includes an air cylinder 68 located beneath the braider plate 58 and a magazine 70 for holding a plurality of cartridges that are pre-loaded with barbed inserts. In one embodiment, the air cylinder preferably serves as an actuator to move the cartridges.

Referring to FIG. 1, the automated braider system 50 also preferably includes a fiber optic sensor display 72 and a cartridge insertion rod 74 for advancing loaded cartridges, one at a time, into the enclosed area 54. The automated braider system 50 also desirably includes a lifting rack 76 that is moveable in a first direction (e.g., up) for advancing a loaded cartridge toward the braider eyelet 62, and in a second direction (e.g., down) for dispensing an empty cartridge from the automated system. The air cylinder may be coupled with the lifting rack.

The braider system 50 also desirably includes a cartridge ejection tube 78 for dispensing empty cartridges from the system after barbed inserts have been withdrawn from the cartridges by the braider system, and preferably after the cartridges have been returned to a position below the braider plate 58 by the lifting rack 76. The braider system also desirably includes a suture core 80, which provides increased tensile strength and controls elongation of the braided suture.

In one embodiment of the present invention, barbed inserts are loaded into cartridges and the loaded cartridges are advanced into the enclosed area 54 of the automated braider system. Once the barbed inserts are advanced into the enclosed area, filaments are preferably wound around the barbed inserts to make braided barbed sutures. The barbed inserts and filaments may be made of biocompatible absorbable materials, non-absorbable materials, and combinations of absorbable and non-absorbable materials. Preferred non-absorbable materials suitable for both the barbed inserts and the filaments are polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons, etc. and the like, or copolymers of combinations thereof. Preferred absorbable polymeric materials suitable for both the barbed inserts and the filaments include polydioxanone, polyglactin, polyglycolic acid, copolymers of glycolide and lactide, polyoxaesters, and poliglecaprone. In certain preferred embodiments, these may include combinations of both absorbable and non-absorbable materials, especially for the filaments. In addition, metals or ceramics may be suitable for certain applications, such as instances where specific strength or corrosion resistance is necessary. In one preferred embodiment, the preferred material is a polymer blend of polyvinylidene fluoride and polyvinylidene fluoride-co-hexafluoropropylene material. In a highly preferred embodiment, the filament material is polyethylene terephthalate. In addition, any of these materials may have conventional surface modifications that include coatings, plasma treatments, therapeutics and the like.

Figure 2:
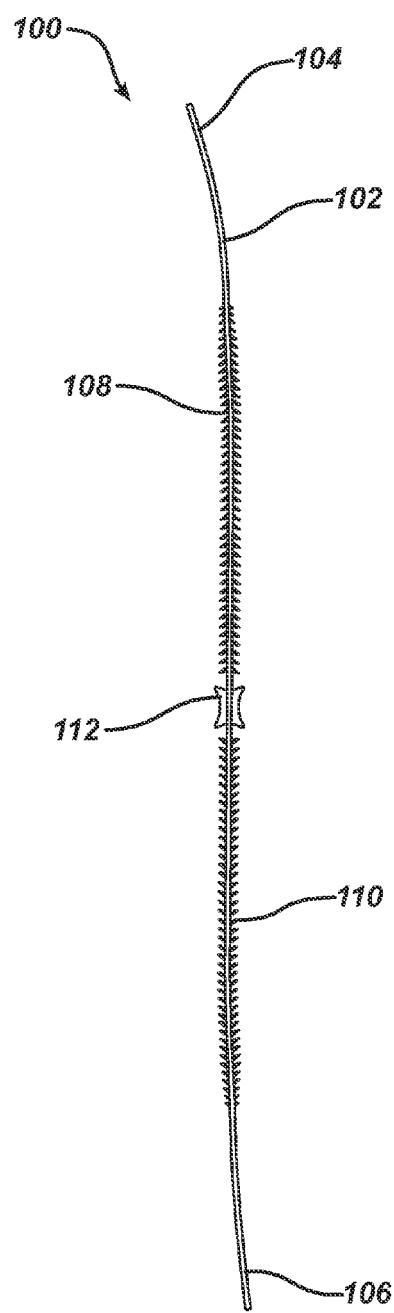
FIG. 2 shows a barbed insert used for making a braided barbed suture, in accordance with one embodiment of the present invention.

Referring to FIG. 2, in one embodiment, a barbed insert 100 includes a core 102 extending between a first end 104 and a second end 106 of the barbed insert. In one embodiment, the barbed insert 100 includes a first set of barbs 108 extending in a first direction and a second set of barbs 110 extending in a second direction that is opposite the first direction, thereby providing a bi-directional barbed insert. In one embodiment, the barbed insert 100 preferably includes a pledget stopper 112 located between the first set of barbs 108 and the second set of barbs 110. The pledget stopper preferably prevents the barbed insert from being pulled too far in one direction.

Figure 3:
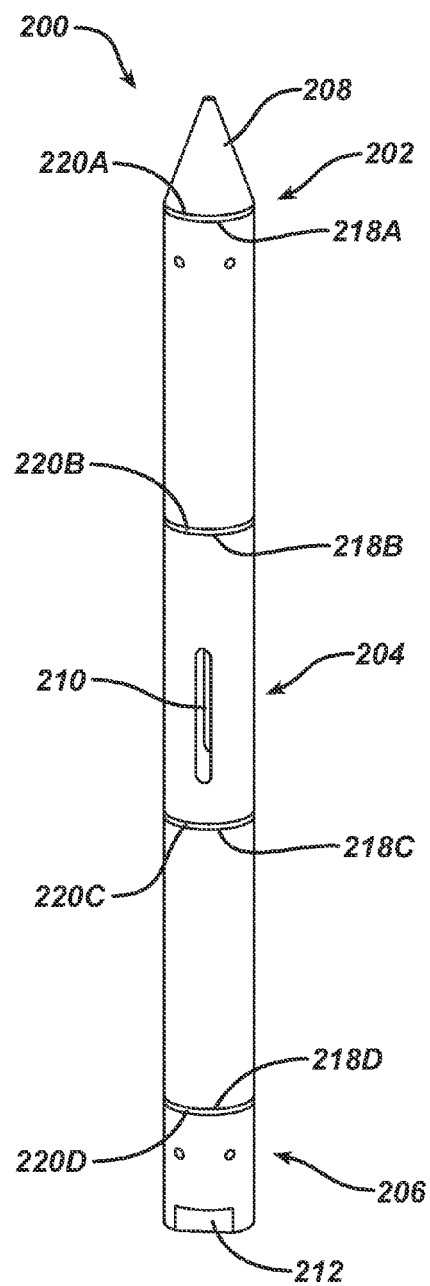
FIG. 3 shows a cartridge used for making braided barbed sutures, in accordance with one embodiment of the present invention.

Referring to FIG. 3, in one embodiment, the barbed insert shown in FIG. 2 is pre-loaded into a cartridge 200. In one embodiment, the cartridge 200 is made of a durable material such metal. In one embodiment, the cartridge 200 is preferably made of stainless steel. Preferred materials for the cartridge include stainless steel, polyvinyl chloride, nylon, and polyoxymethylene (e.g. DELRIN thermoplastic acetal resin). In one embodiment, the cartridge 200 has an upper end 202, an intermediate section 204 and a lower end 206. The upper end 202 of the cartridge preferably defines a leading point or tip 208. As will be described in more detail below, the leading point 208 at the upper end 202 of the cartridge 200 desirably includes an opening or passageway for receiving the barbed insert 100 shown in FIG. 2. The cartridge 200 preferably includes an optical window 210 extending through the cartridge. The optical window 210, which may be located in the intermediate section 204 of the cartridge 200, preferably provides visual access to the barbed insert loaded in the cartridge. The lower end 206 of the cartridge 200 preferably has a keyed end 212, which enables the lower end 206 to be connected with the cartridge insertion rod 74 (FIG. 1), as will be described in more detail below.

Figure 4A:
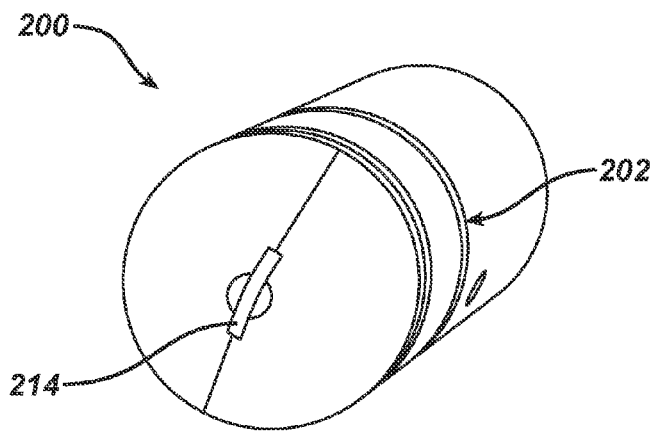
FIG. 4A shows a top view of the cartridge shown in FIG. 3.
Figure 4B:
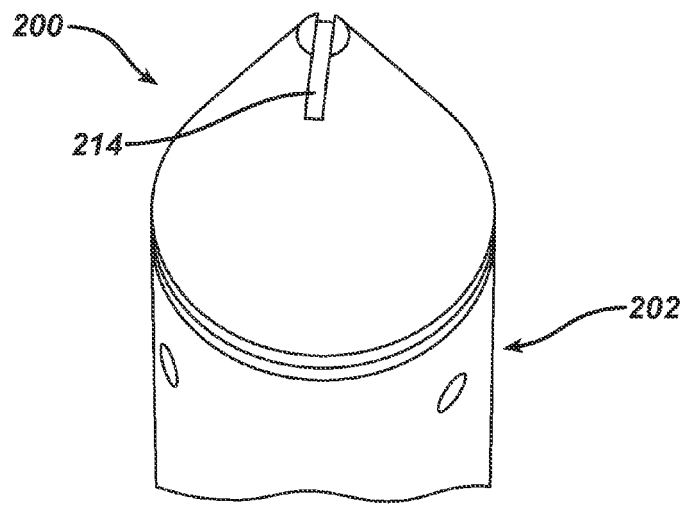
FIG. 4B shows a top perspective view of the cartridge shown in FIGS. 3 and 4A.

Referring to FIGS. 4A and 4B, in one embodiment, the cartridge 200 includes an opening 214 at the leading end 202 thereof that defines a passageway for orienting a barbed insert. In one embodiment, the passageway preferably defines an elongated slit that is sized and shaped to closely conform to the cross-sectional shape of the barbed insert 100 shown in FIG. 2. The elongated slit 214 desirably has a dimension that enables the barbs of the barbed insert to slide into the slit, while preventing the barbed insert from rotating about its longitudinal axis relative to the longitudinal axis of the cartridge 200.

In one embodiment, the barbed insert has barbs that are oriented at 180 degrees from one another. This orientation lends itself to having the cartridge opening accommodate barbs at 180 degrees from one another by having a cartridge opening that is shaped as an elongated slit (having a width greater than its height). However, the orientation of the barbed inserts is not limited to having barbs that are 180 degrees opposed from one another. An example would be a barbed insert having three sets of barbs, whereby each set of barbs is oriented 120 degrees from each other around the axis of the core. In this embodiment, the barbed insert dispenser opening of the cartridge may have a cross-section that accommodates this arrangement in a manner to maintain rotational alignment and prevent undesired rotation of the barbed insert around its core while allowing for longitudinal motion of the insert as it is drawn into the winding filaments. In one embodiment, systems and methods for making braided barbed sutures include loading one barbed insert into one barbed insert dispenser opening in preparation for its delivery into the winding filaments. In one embodiment, however, a single cartridge may have multiple openings/cross-sections to accommodate one barbed insert per cartridge opening or multiple barbed inserts in a single cartridge opening.

Figure 5A:
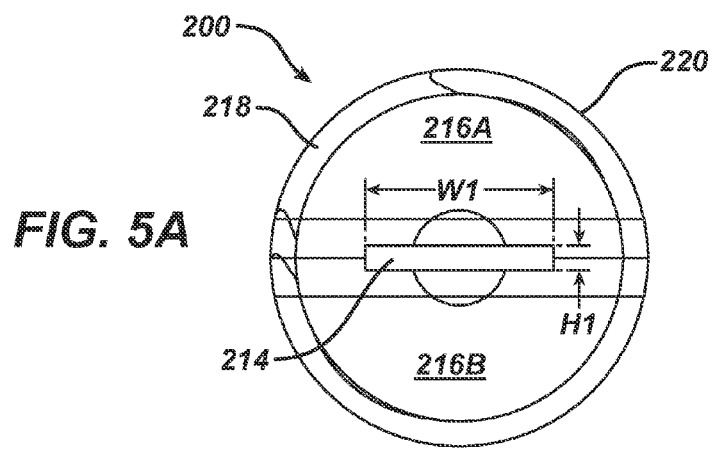
FIG. 5A shows a cross-sectional view of a cartridge used for making braided barbed sutures, in accordance with one embodiment of the present invention.

Referring to FIG. 5A, in one embodiment, the cartridge 200 includes a first elongated half 216A and a second elongated half 216B that are adapted to be assembled together. Outer surfaces of the first and second elongated halves 216A, 216B define at least one annular groove 218 formed therein, and a C-shaped ring 220 is positionable in the at least one annular groove 218 for holding the first and second elongated halves 216A, 216B together. The elongated halves 216A, 216B have opposing grooves formed therein. When assembled together, the opposing grooves of the first and second elongated halves 216A, 216B cooperatively define an elongated slit 214. In one embodiment, the elongated slit has a width $W_1$ of about 0.030-0.080 inches and a height $H_1$ of about 0.0075-0.0125 inches.

Figure 5B:
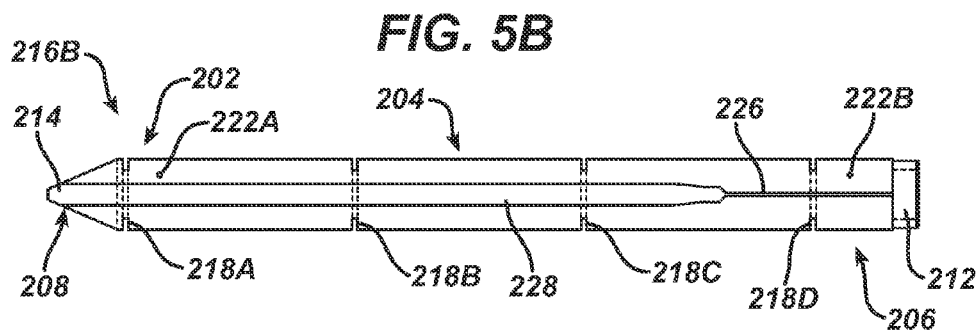
FIG. 5B shows another cross-sectional view of the cartridge shown in FIG. 5A.

FIG. 5B shows the second elongated half 216B of the cartridge 200 shown in FIG. 5A. As noted above, the second elongated half 216B is assembled the first elongated half 216A (FIG. 5A). During assembly of the first and second halves together, the first and second halves are held together by positioning C-shaped rings 220, shown in FIG. 5A, within the annular grooves 218A-218D provided along the length of the elongated halves. In the embodiment shown in FIG. 5B, the second cartridge half 216B includes pin openings 222A, 222B adapted to receive opposing pins projecting from the first elongated half of the cartridge. The second elongated half 216B of the cartridge 200 includes an upper end 202 having a leading tip 208, an intermediate section 204, and a lower end 206 having a keyed end 212.

The second elongated half 216B of the cartridge 200 has one of the opposing grooves formed therein that defines the elongated slit 214. In one embodiment, the opposing groove that defines the elongated slit 214 preferably extends from the leading end 202 of the cartridge to the keyed end 212 of the cartridge 200. In one embodiment, the groove that defines the slit 214 includes a narrower stem-shaped section 226 that accommodates the core of the barbed insert at the second end 104 of the barbed insert. A main section 228 of the slit 214 is wider than the stem-shaped section 226 and is sized and shaped to accommodate the barbs on the first and second barbed sections of the barbed insert.

Figure 5C:
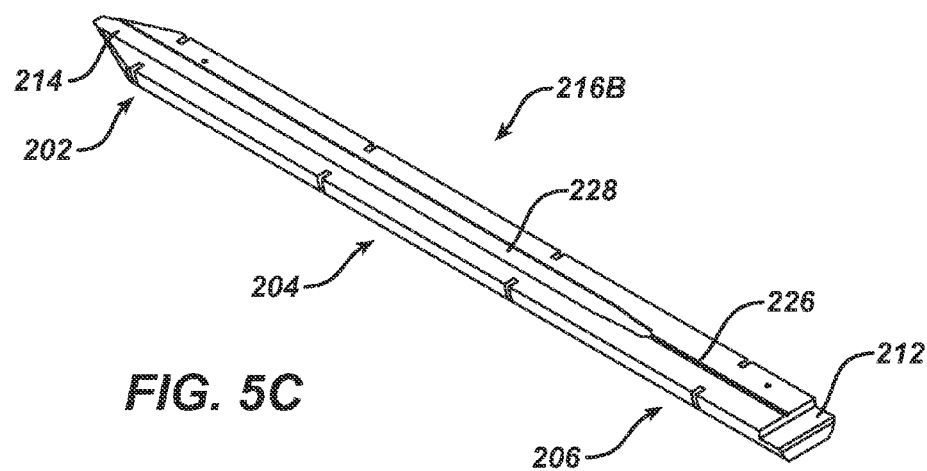
FIG. 5C shows a perspective view of the cartridge shown in FIG. 5B.

FIG. 5C shows a perspective view of the second elongated half 216B of the cartridge 200 shown in FIG. 5B. The second elongated half 216B includes the leading end 202 having the leading tip 208 with the slit opening 214 being accessible at the leading tip. The elongated slit 214 preferably extends between the leading end 202 of the cartridge and the stem 226. In one embodiment, the groove that defines the elongated slit 214 desirably has a shape that conforms to the shape of the barbed insert 100 shown in FIG. 2. As noted above, a groove that defines the elongated slit 214 is also preferably formed in the first elongated half 216A of the cartridge 200 shown in FIG. 5A. The elongated slit 214 formed in the cartridge preferably enables the barbed insert to move relative to the cartridge along its longitudinal axis as it is drawn from the slit 214. However, because the shape of the slit closely conforms to the shape of the barbed insert, the slit prevents the section of the barbed insert in contact with the slit from rotating or twisting about its longitudinal axis relative to the slit.

Referring to FIG. 6A, in one embodiment, a barbed insert 100, such as that shown and described above in FIG. 2, is pre-loaded into the cartridge shown and described above in FIGS. 5A-5C. The cartridge 200 includes the elongated slit 214 having a wider leading section 228 adapted to accommodate the first and second barbed sections 108, 110 of the barbed insert 100 and a narrower stem-shaped section 226 adapted to accommodate the core of the barbed insert 100 located at the second end 106 of the barbed insert.

Referring to FIG. 6B, in one embodiment, the leading end 104 of the barbed insert 100 projects from the slit opening 214 at the leading end 202 of the cartridge 200. The barbs of the first barbed section 108 are desirable disposed within the wider section 228 of the slit 214. In one embodiment, the barbed insert 100 is loaded into the cartridge 200 by moving the barbed insert in a direction indicated $D_1$. During a braiding operation, the barbed insert 100 may move in the direction $D_2$ as it is withdrawn from the slit 214 at the leading end 202 of the cartridge 200.

Referring to FIG. 6C, in one embodiment, the trailing end of the elongated groove 222 tapers inwardly to closely match and conform to the configuration of the barbs of the second barbed section 110 of the barbed insert 100. The core at the second end 106 of the barbed insert 100 fits within the narrower stem-shaped groove 226 formed adjacent the lower end 206 of the cartridge 200.

FIG. 6D shows the elongated slit opening 214 provided at the leading tip 208 of the cartridge 200. As shown in FIG. 6D, the size and shape of the elongated slit opening closely matches the cross-sectional size and shape of the barbed insert 100. The barbs on the barbed insert 100 preferably have a wing span that closely matches the width $W_1$ of the slit 214. The core 102 of the barbed insert 100 is desirably centered within the slit 214. Because the dimensions of the elongated slit 214 closely match the outer dimensions of the barbed insert 100, the barbed insert is prevented from rotating about its longitudinal axis relative to the slit by the inner surfaces of the slit 214. As such, the barbed insert 100 is only capable of moving longitudinally relative to the longitudinal axis of the cartridge. Although the present invention is not limited by any particular theory of operation, it is believed that providing a narrow, elongated slit opening 214 at the leading end of the cartridge 200 better controls the movement and orientation of the barbed insert 100 relative to the cartridge 200. As a result, undesirable twisting and bending of the barbed insert 100 may be eliminated.

Figure 7A:
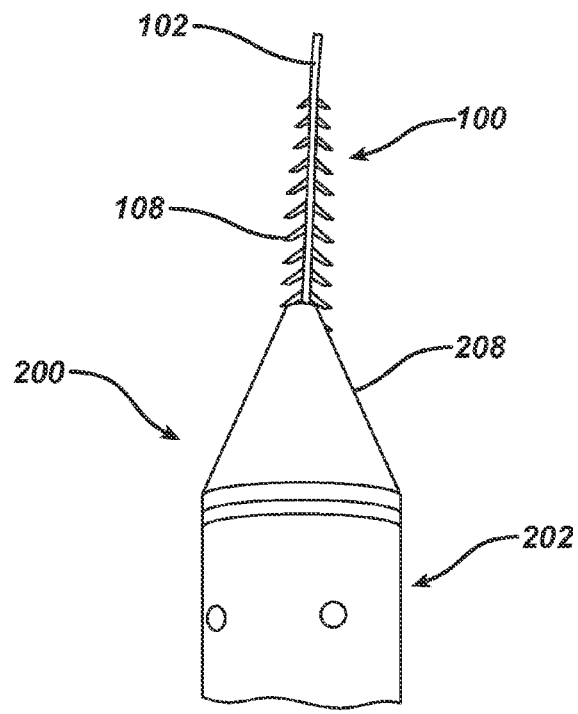
FIG. 7A shows a side view of the cartridge of FIG. 3 loaded with the barbed insert of FIG. 2.

Referring to FIG. 7A, in one embodiment, the barbed insert 100 is loaded into the elongated slit opening 214 at the leading end 202 of the cartridge 200 so that the first end 102 of the barbed insert 100 projects from the elongated slit. In FIG. 7A, the first barbed section 108 of the barbed insert 100 projects from the leading tip 208 of the cartridge 200. In at least one embodiment, however, the barbs of the first barbed section 108 are preferably fully inserted within the elongated slit of the cartridge so that only the stem or core at the first end 102 of the barbed insert is exposed.

Figure 7B:
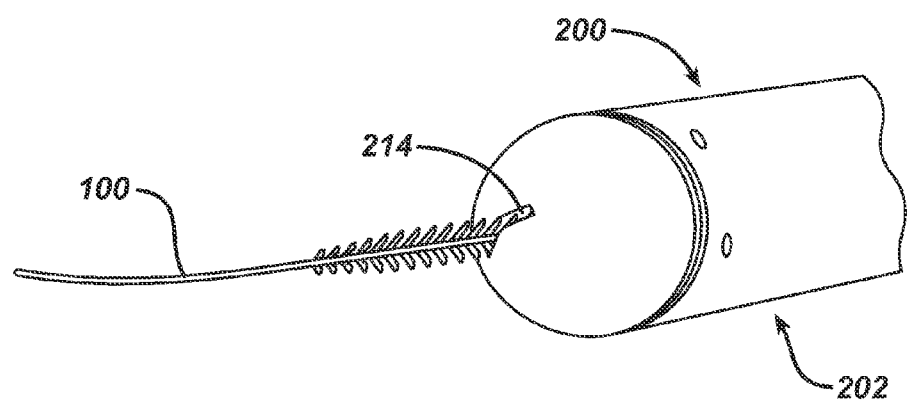
FIG. 7B shows a top perspective view of the cartridge and the barbed insert shown in FIG. 7A.

FIG. 7B shows the elongated slit opening 214 at the leading end 202 of the cartridge 200. The elongated slit opening 214 preferably accommodates the barbs on the barbed insert 100. The elongated slit opening 214 is sized and shaped to receive the barbs and be in relatively close conformance with the outer perimeter of the barbed insert 100 to prevent the barbed insert from rotating or twisting about its longitudinal axis relative to the cartridge when the barbed insert is loaded into the cartridge 200.

Figure 7C:
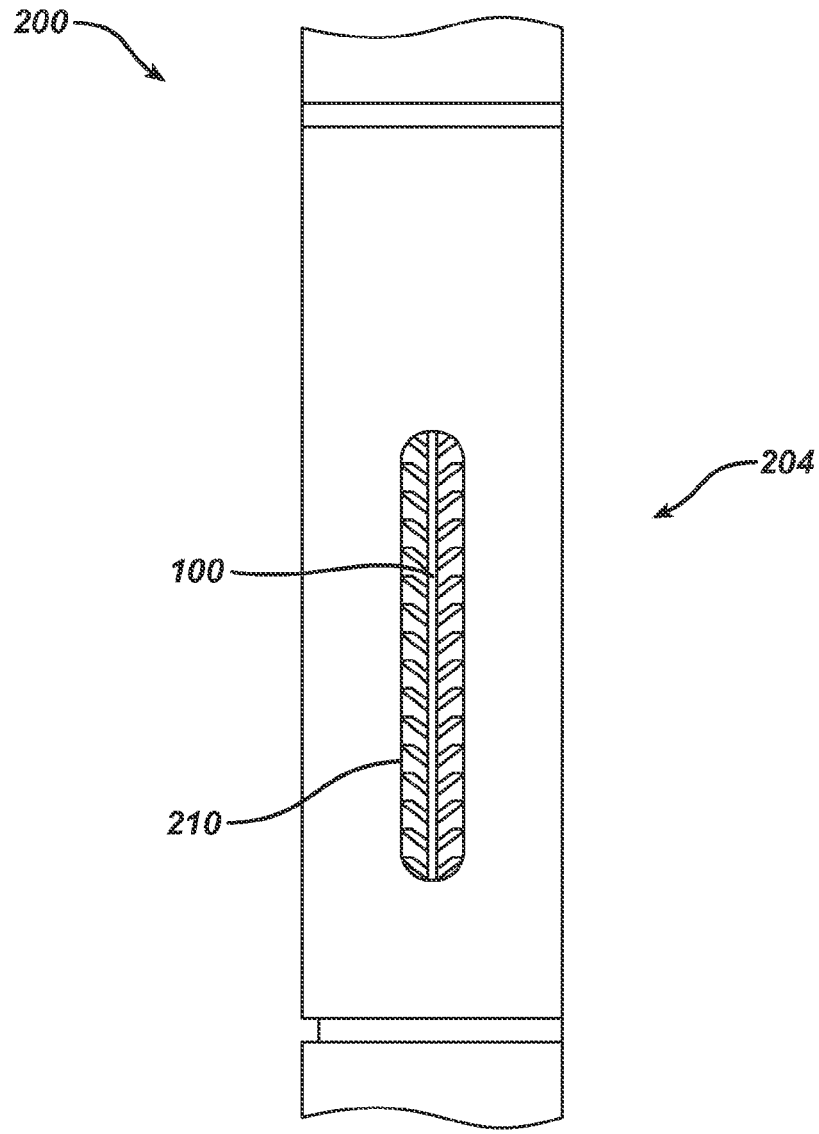
FIG. 7C shows a mid-section of the cartridge of FIG. 3 with the barbed insert visible through an optical window, in accordance with one embodiment of the present invention.

Referring to FIG. 7C, in one embodiment, the cartridge 200 includes an optical window 210 that provides a view of the barbed insert 100 when the insert is disposed in the cartridge. The optical window may be located in the intermediate section 204 of the cartridge 200. As will be described in more detail herein, the automated braider system of the present invention preferably includes an optical sensor adapted to determine when the barbed insert has been completely dispensed from the cartridge 200. In one embodiment, once the barbed insert has been completely dispensed, the optical sensor will send at least one signal to a system controller indicating that the barbed insert has been dispensed. In response, the system controller will preferably issue commands for retracting the empty cartridge 200 below the braider plate and discharging the empty cartridge from the system so that another cartridge loaded with a barbed insert may be advanced into place for braiding.

Referring to FIG. 8A, in one embodiment, the lower end 206 of the cartridge 200 has a keyed end 212 formed therein. In one embodiment, the keyed end 212 preferably includes a first projection 230, a second projection 232 spaced from the first projection 230, and a central gap 234 extending between the first and second projections 230, 232. In one embodiment, the keyed end 212 enables the lower end 206 of the cartridge 202 to be engaged by an upper end of the cartridge insertion rod 74 (FIG. 1). The upper end of the cartridge insertion rod may also be keyed for meshing with the keyed lower end 212 of the cartridge 200. The meshing of the upper end of the cartridge insertion rod with the lower end of the cartridge preferably provides better control of the cartridge. For example, in one embodiment, it may be desirable to prevent rotation of the cartridge about its longitudinal axis during a filament winding operation. In other embodiments, however, it may be desirable to rotate the cartridge about its longitudinal axis during a filament winding operation. For example, the cartridge may be rotated about its longitudinal axis as filaments are wound about a barbed insert. As the cartridge rotates about its longitudinal axis, the barbed insert loaded in the cartridge will also be rotated about its longitudinal axis so that the filaments are helically wound about the core of the barbed insert so that the barbs project 360° about the longitudinal axis of the braided barbed insert.

Figure 8B:
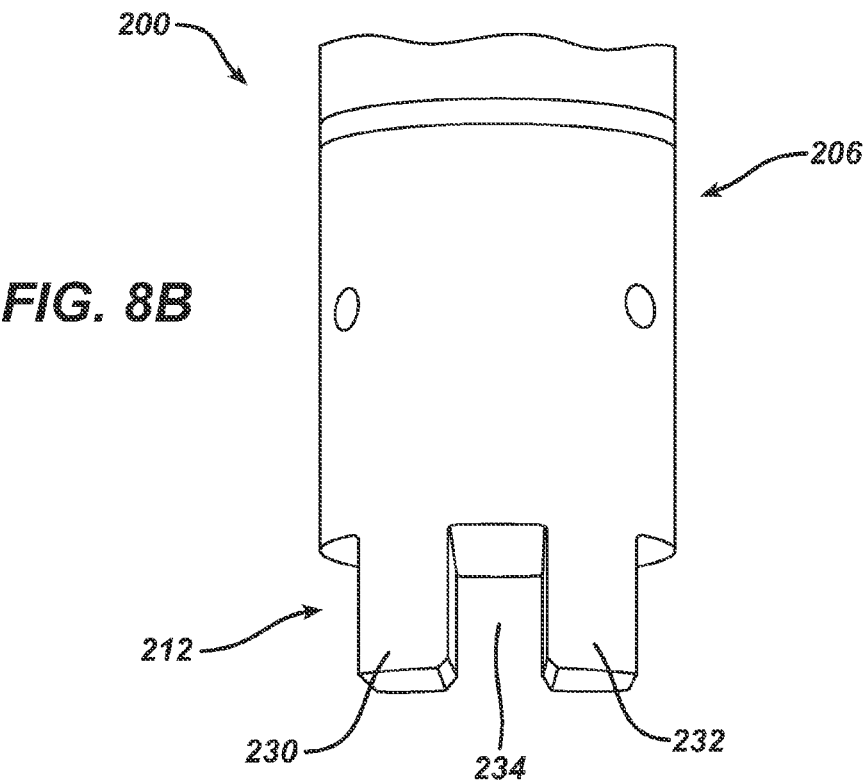
FIG. 8B shows a side view of the lower end of the cartridge of FIG. 8A.

FIG. 8B shows a side view of the lower end 206 of the cartridge 200. The keyed lower end 212 includes the first projection 230 spaced from the second projection 232 to define the central gap 234. The keyed lower end 212 desirably enables the lower end 206 of the cartridge 200 to mesh with an upper end of a cartridge insertion rod.

Figure 8C:
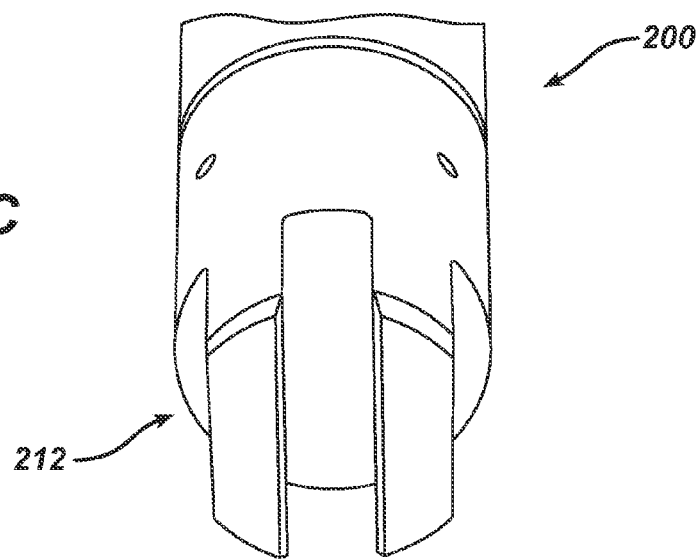
FIG. 8C shows a perspective end view of the lower end of the cartridge shown in FIGS. 8A and 8B.

FIG. 8C shows an end view of the keyed lower end 212 of the cartridge 200. Although a particular keyed structure is shown in FIGS. 8A-8C, the present invention contemplates that other structures or connecting structures may be used. Although the present invention is not limited by any particular theory of operation, it is believed that providing a keyed structure at the lower end 206 of a cartridge 200 enables better control of the cartridge. In one embodiment, the keyed structure is utilized to prevent rotation of the cartridge about its longitudinal axis so that the cartridge only moves in axial directions along its longitudinal axis, which, in turn, prevents the barbed insert loaded therein from rotating about its longitudinal axis. In one embodiment, the keyed structure enables the cartridge to be rotated about its longitudinal axis, which, in turn, rotates the barbed insert about its longitudinal axis to form braided barbed sutures that are helically wound with barbs projecting 360° about the longitudinal axis of the suture. In these latter embodiments, the keyed structure enables the cartridge to be simultaneously rotated about its longitudinal axis while being moved in axial directions along its longitudinal axis.

Figure 9:
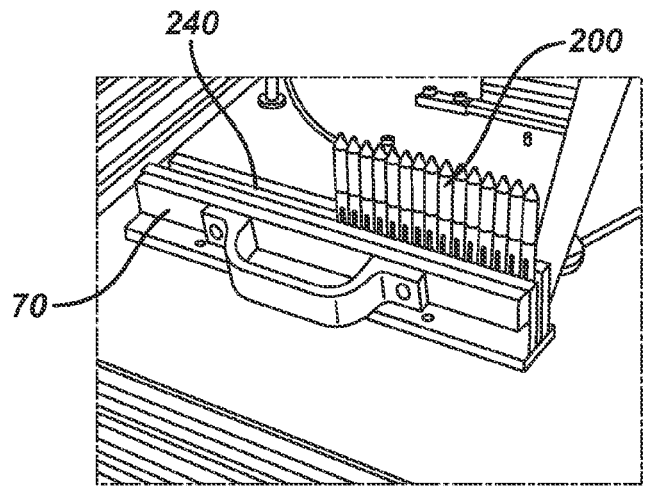
FIG. 9 shows a magazine holding a plurality of cartridges, in accordance with one embodiment of the present invention.

Referring to FIG. 9, in one embodiment, an automated system includes a magazine 70 having an elongated slot 240 adapted to hold a plurality of cartridges 200 pre-loaded with barbed inserts. In one embodiment, the cartridges 200 are loaded into the magazine 70 so that the lower ends of the cartridges are positioned within the elongated slot 240 of the magazine 70 and the upper ends of the cartridge are in substantial alignment with one another and spaced from the elongated slot 240.

Figure 10:
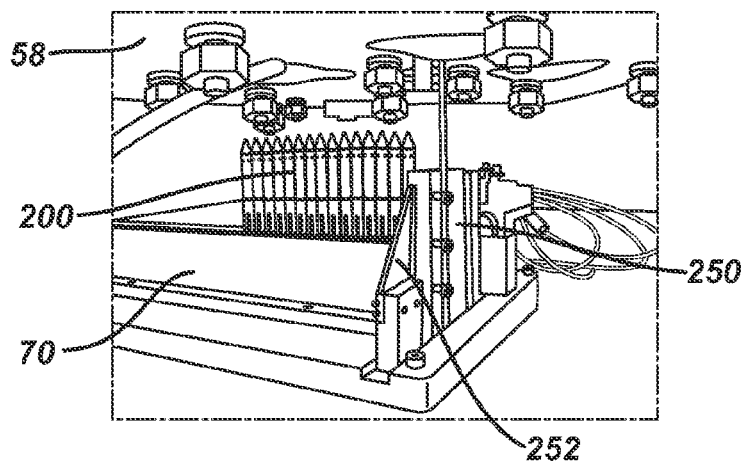
FIG. 10 shows the magazine and cartridges of FIG. 9 positioned beneath a braider plate of the system shown in FIG. 1, in accordance with one embodiment of the present invention.

Referring to FIG. 10, in one embodiment, the magazine 70 has a plurality of cartridges 200 loaded therein and is positioned below the braider plate 58. The system includes a cartridge chamber 250 that is adapted to receive a leading cartridge. The cartridge chamber 250 preferably has an opening that is sized and shaped to conform to the outer surface of the cartridge 200 when the cartridge is received therein. When the lead cartridge is advanced into the opening of the cartridge chamber 250, the cartridge chamber 250 is preferably adapted to position the leading cartridge in alignment with the cartridge insertion rod 74 (FIG. 1). The braider system also desirably includes a retractable gate 252 that is moveable between open and closed positions. When the retractable gate 252 is in the open position, a leading cartridge may be loaded into the cartridge chamber 250. When the retractable gate 252 is in a closed position, the gate prevents any cartridges from being advanced into the cartridge chamber 250.

Figure 11A:
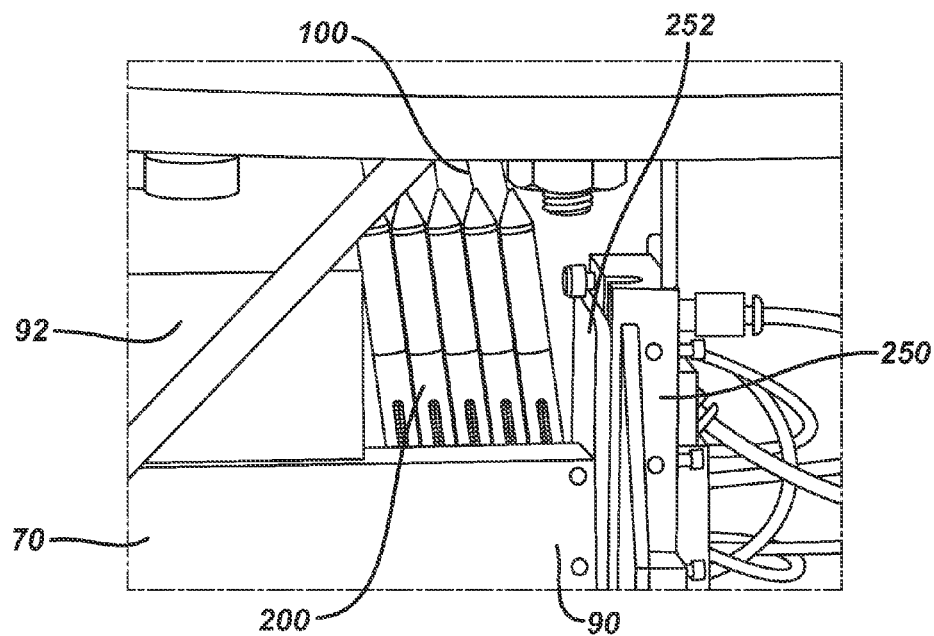
FIGS. 11A-11E show a method of loading a cartridge into a system for making braided barbed sutures, in accordance with one embodiment of the present invention.

Referring to FIG. 11A, in one embodiment, the magazine 70 preferably holds a plurality of cartridges 200 having barbed inserts 100 pre-loaded in each of the respective cartridges. The magazine 70 has a leading end 90 that may be aligned with the opening of the cartridge chamber 250. The braider assembly desirably includes a magazine advancer 92 that selectively urges a leading one of the cartridges 200 into the cartridge chamber 250.

Figure 11B:
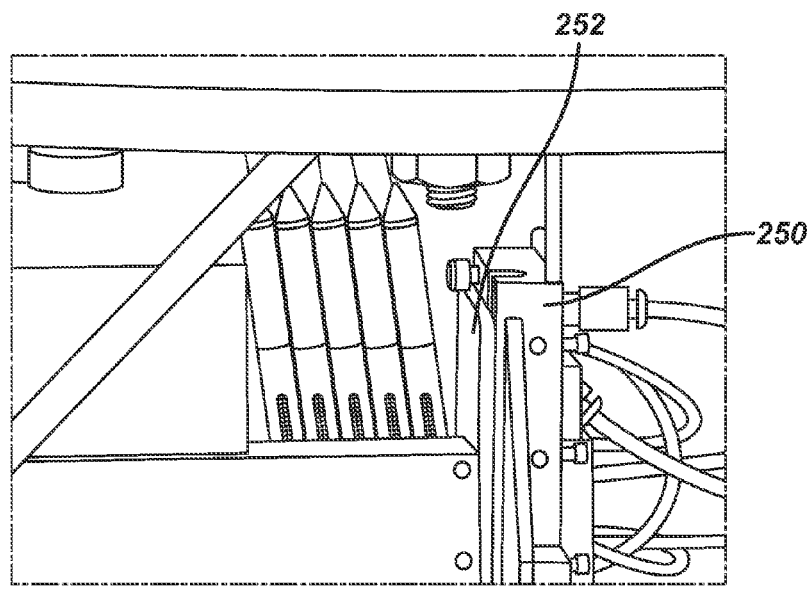

The braider system includes the retractable gate 252 that selectively opens and closes the cartridge chamber 250. In FIG. 11A, the retractable gate 252 is in a closed position so that a lead cartridge 200 may not be advanced into the cartridge chamber by the magazine advancer 92. Referring to FIG. 11B, the retractable gate 252 may be moved into an open position so that the lead cartridge 200 may be advanced into the cartridge chamber 250.

Figure 11C:
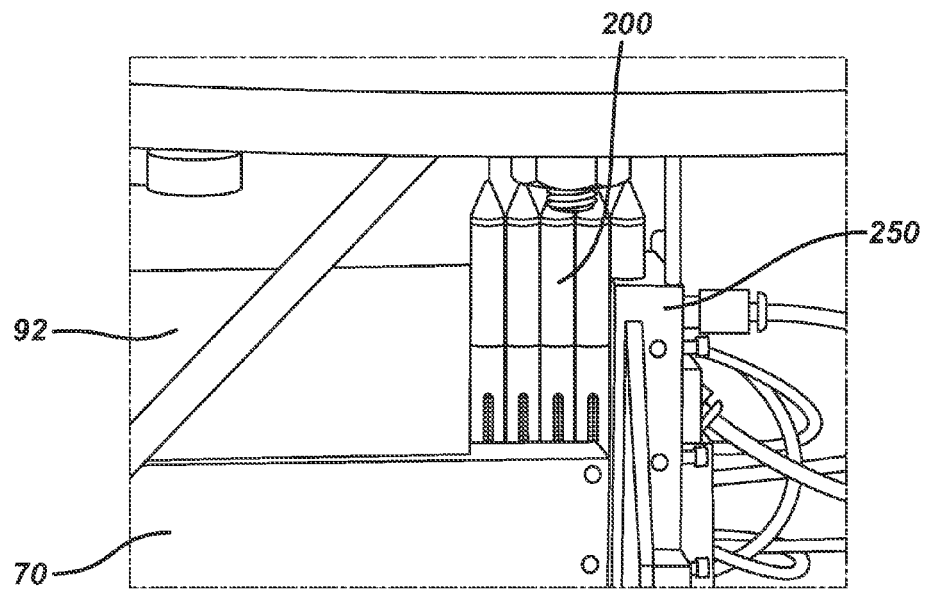
Figure 11D:
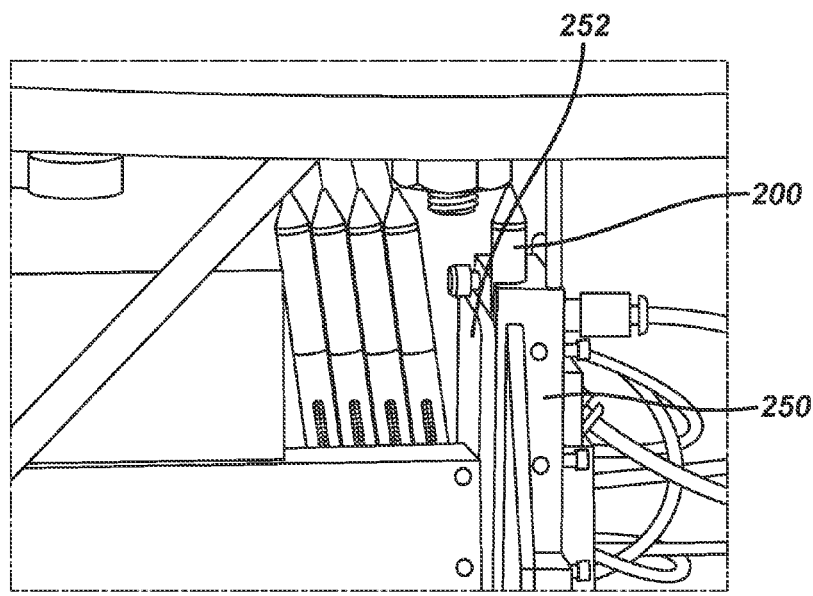

FIG. 11C shows the magazine advancer 92 moving to the right relative to the magazine 70 to advance the lead cartridge 200 into the cartridge chamber 250. Referring to FIG. 11D, after the lead cartridge 200 is advanced into the cartridge chamber 250, the retractable gate 252 returns to the closed position.

Figure 11E:
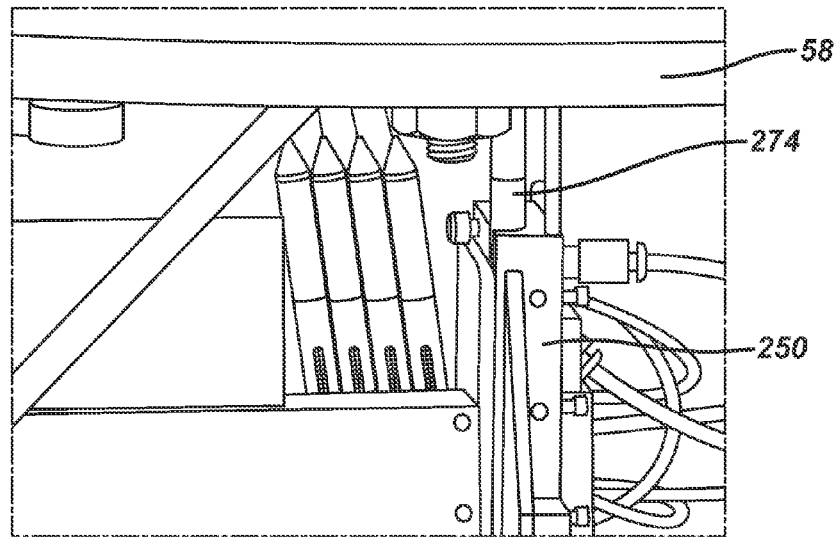

Referring to FIG. 11E, after the lead cartridge has been advanced into the cartridge chamber 250 and the retractable gate 252 is closed, the cartridge insertion rod 74 preferably engages the cartridge for advancing the pre-loaded cartridge through the braider plate 58 and into the enclosed area 54 (FIG. 1) of the automated system.

Figure 12:
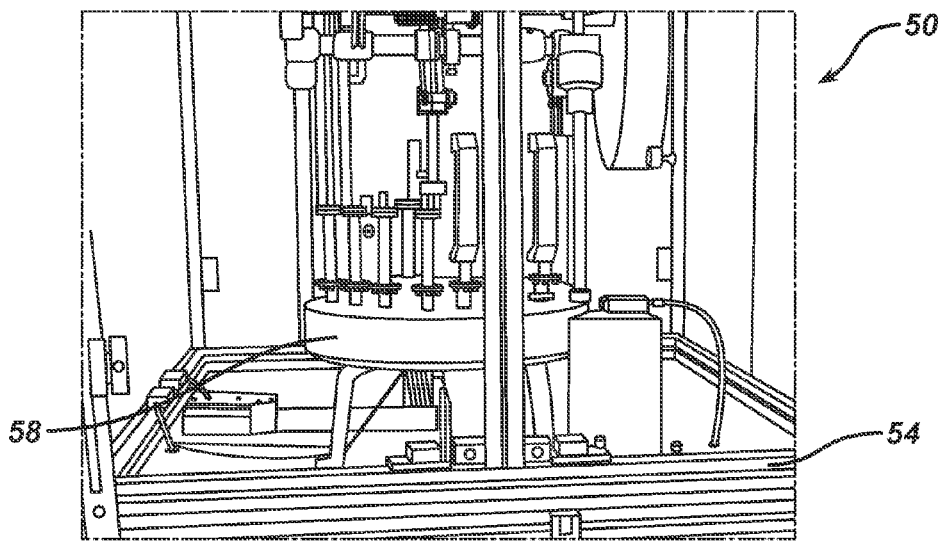
FIG. 12 shows the system of FIG. 1 during the method step shown in FIG. 11E, in accordance with one embodiment of the present invention.

Referring to FIG. 12, in one embodiment, the cartridge insertion rod 58 advances the pre-loaded cartridge into the enclosed area 54 of the automated braider system 50 so that filaments may be wound about the barbed insert loaded in the cartridge to form a braided barbed suture.

Figure 13:
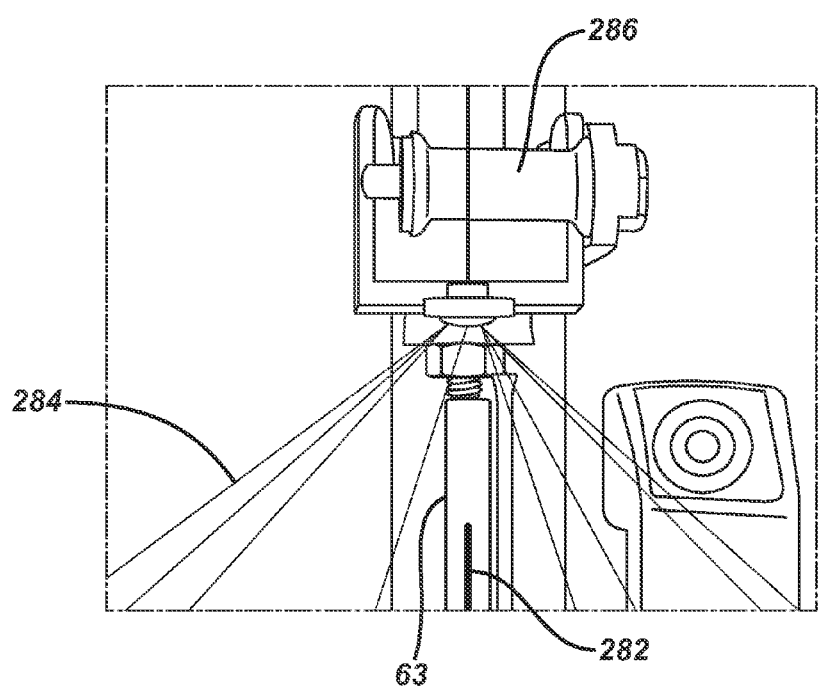
FIG. 13 shows a cartridge guide tube and a filament winding assembly, in accordance with one embodiment of the present invention.

Referring to FIG. 13, in one embodiment, the braider system includes a filament winding assembly including a braider eyelet 62 and a cartridge guide tube 63 that preferably aligns the upper end of the cartridge with the braider eyelet 62. The braider system includes a fiber optic sensor 282 that detects the presence or absence of a barbed insert in the cartridge. The braider system includes a plurality of suture bobbins that provide filaments 282 that are wound about the barbed insert to form a braided barbed suture. The braider system also preferably includes a rotatable spool 286 that guides downstream advancement of the braided barbed sutures after the filaments have been wound about the barbed insert.

Figure 14A:
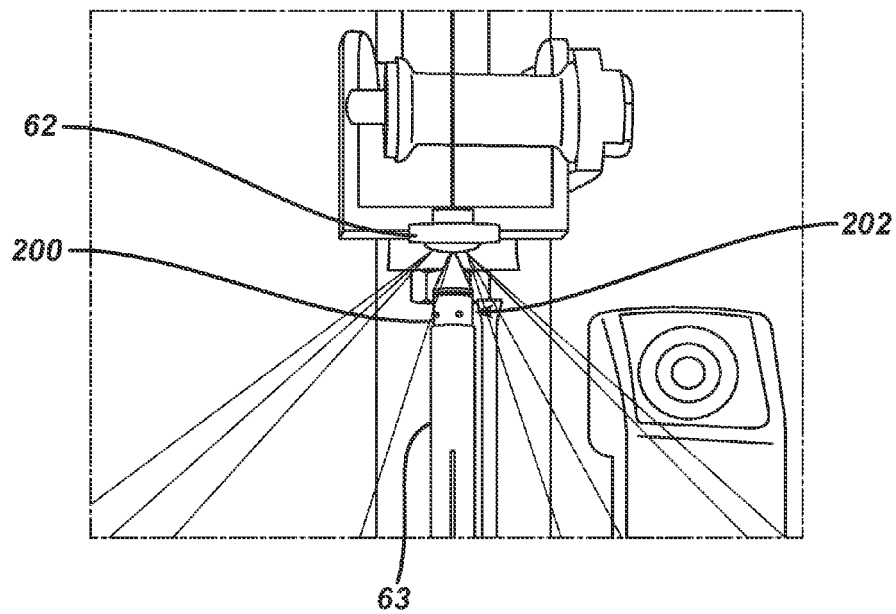
FIGS. 14A and 14B show a method of advancing an upper end of a cartridge toward a filament winding assembly, in accordance with one embodiment of the present invention.

Referring to FIG. 14A, in one embodiment, the cartridge insertion rod advances the cartridge 200 through the cartridge guide tube 63 so that the leading end 202 of the cartridge 200 advances from the upper end of the cartridge guide tube 63 and into alignment with the braider eyelet 62.

Figure 14B:
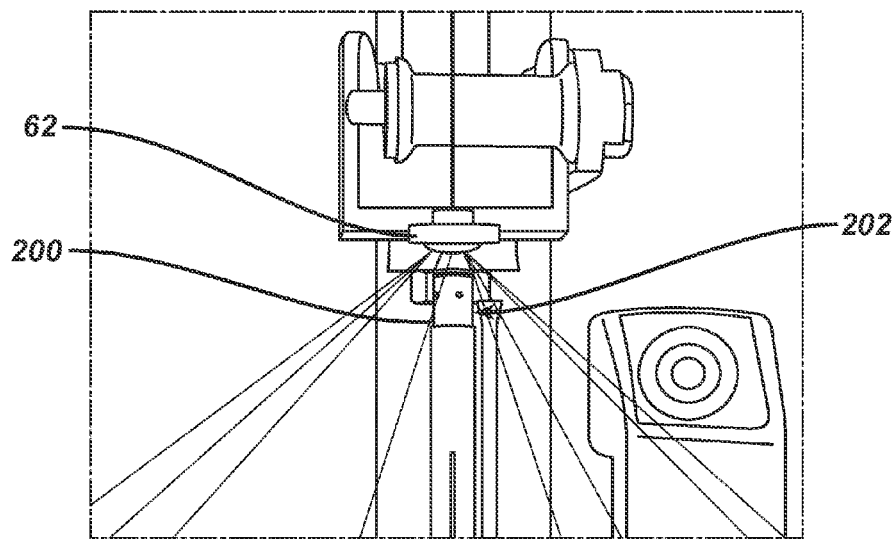
Figure 14C:
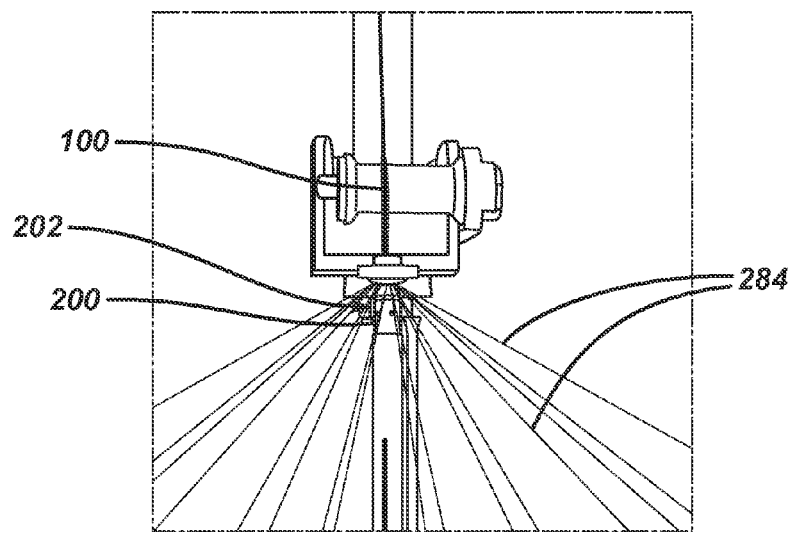
FIG. 14C shows filaments being wound about a barbed insert for forming a braided barbed suture, in accordance with one embodiment of the present invention.

Referring to FIG. 14B, the cartridge insertion rod continues to advance the cartridge 200 upward until the leading end 202 of the cartridge engages the braider eyelet 62. Referring to FIG. 14C, the winding filaments 284 draw the barbed insert 100 from the elongated slit at the leading end of the cartridge 200 and the filaments 284 are wound about the barbed insert 100.

Figure 15:
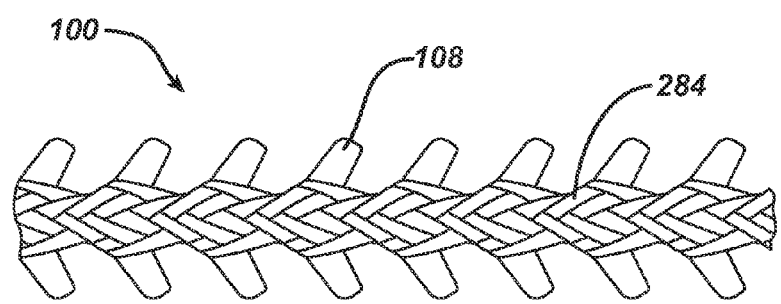
FIG. 15 shows a braided barbed suture, in accordance with one embodiment of the present invention.

Referring to FIG. 15, in one embodiment, the filaments 284 are wound about the core (not shown) of the barbed insert 100 to form a braided barbed suture. In the braided barbed suture of FIG. 15, a plurality of filaments 284 are wound about the suture along the length thereof. The barbs 108 preferably project through the plurality of filaments 284 so that the barbs remain exposed. The barbs 108 preferably lie in a single plane, which preferably results from the barbed insert being held in a single plane by the cartridge as the barbed insert is withdrawn from the cartridge.

Figure 16:
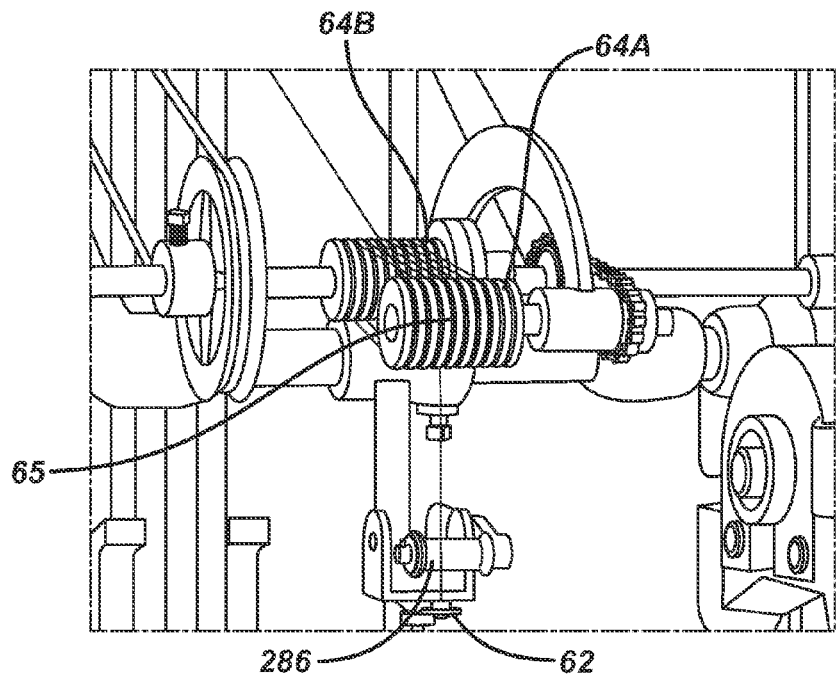
FIG. 16 shows a braider dowel positioned downstream from the filament winding assembly shown in FIG. 14C, in accordance with one embodiment of the present invention.
Figure 17:
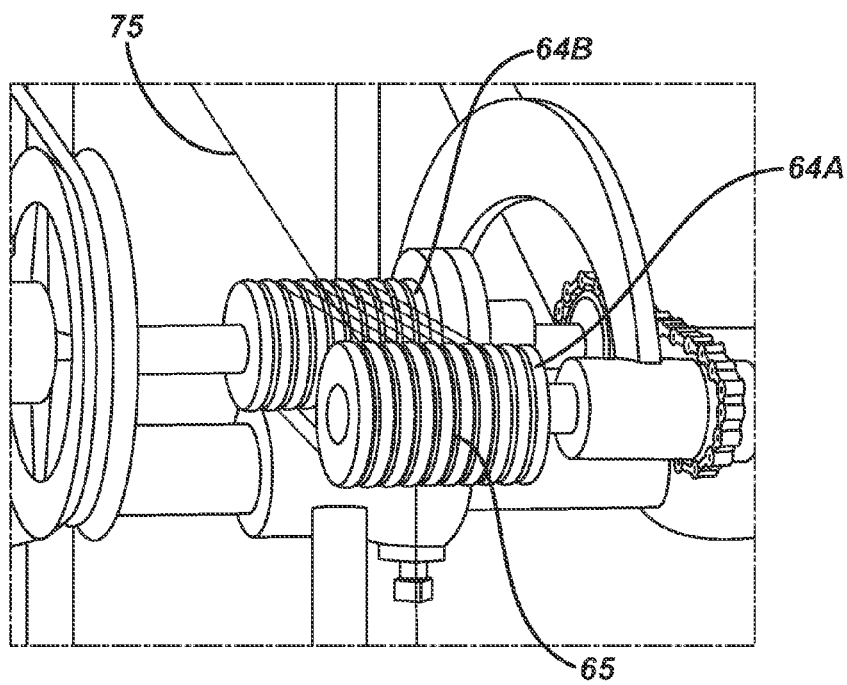
FIG. 17 shows a magnified view of the braider dowel shown in FIG. 16.

Referring to FIG. 16, in one embodiment, the braider system includes a pair of braider dowels 64A, 64B located downstream in the process from the braider eyelet 62 and the rotatable spool 286. Each of the braider dowels 64A, 64B preferably has a helical groove 65 formed therein that is adapted to receive the braid 75 and the braided barbed sutures therein. FIG. 17 shows a braided barbed suture disposed within a helical groove 65 of the first braider dowel 64A. Although the present invention is not limited by any particular theory of operation, it is believed that the pair of braider dowels 64A, 64B effectively maintains tension upon the braid 75 as the braid moves downstream. In one embodiment, the two dowels 64A, 64B are spaced apart and offset from one another so that the suture progressively advances to the next groove as the suture passes back and forth between the two dowels 64A, 64B.

Figure 18:
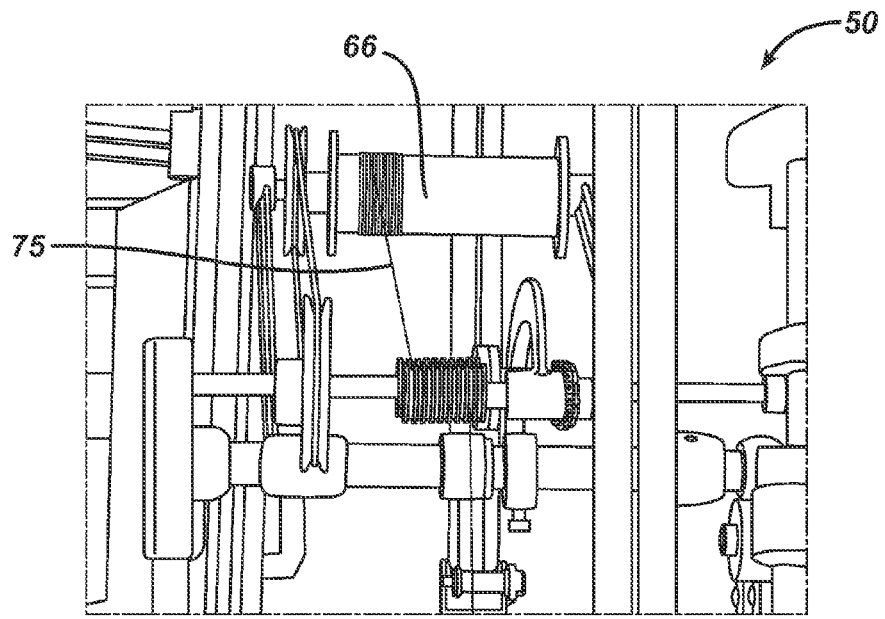
FIG. 18 shows a suture collection spool located downstream from the braider dowel shown in FIGS. 16 and 17, in accordance with one embodiment of the present invention.

Referring to FIG. 18, in one embodiment, the braider system 50 includes the suture collection spool 66 that is adapted to collect the braid 75 and the braided barbed sutures thereon. The suture collection spool 66 preferably rotates to collect the braid 75 and the braided barbed sutures thereon for later handling and use.

Figure 19:
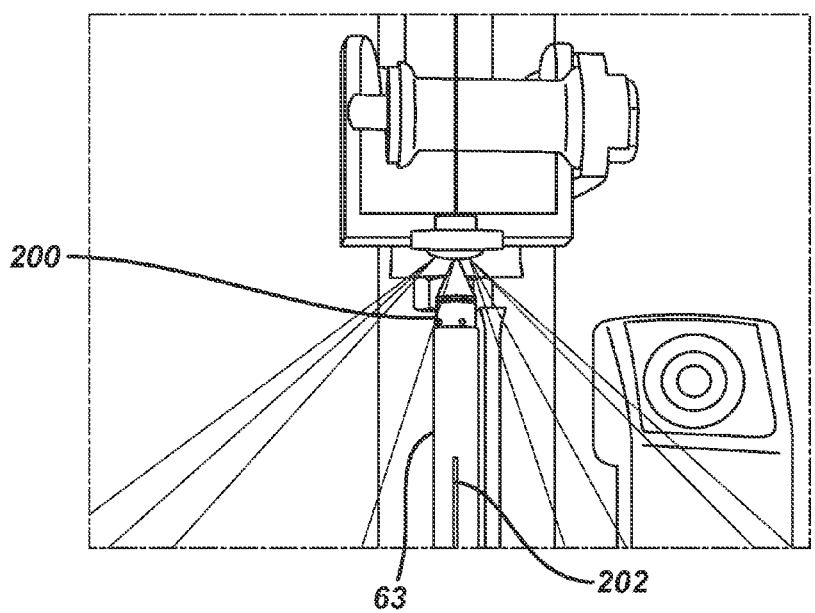
FIG. 19 shows an empty cartridge being dispensed from the system after a barbed insert has been drawn from the cartridge, in accordance with one embodiment of the present invention.

Referring to FIG. 19, in one embodiment, after the barbed insert has been removed from the cartridge 200, the optical sensor 282 detects the absence of the barbed insert. In response, the system controller retracts the cartridge insertion rod, which, in turn, retracts the empty cartridge 200 within the cartridge guide tube 63.

Figure 20A:
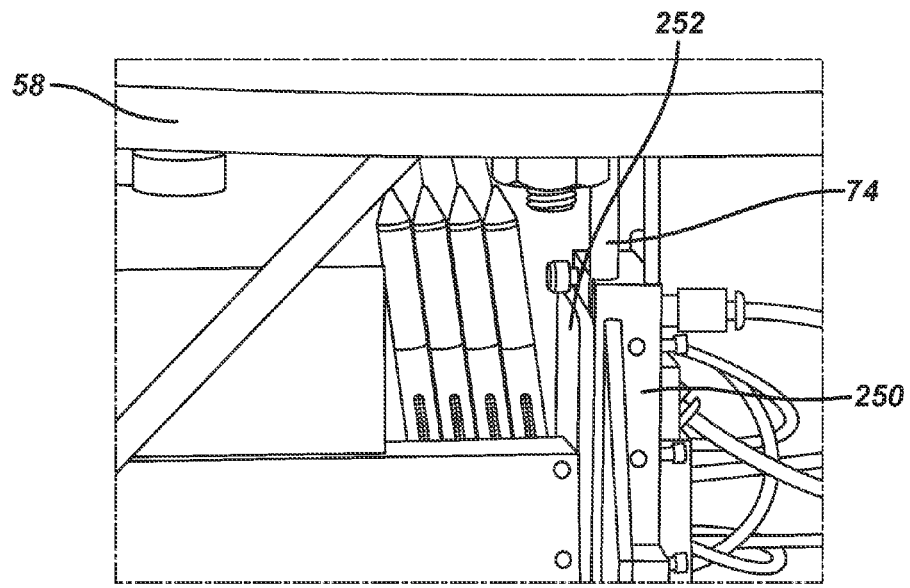
FIGS. 20A-20D show a method of removing an empty cartridge from the system shown in FIG. 1, in accordance with one embodiment of the present invention.
Figure 20B:
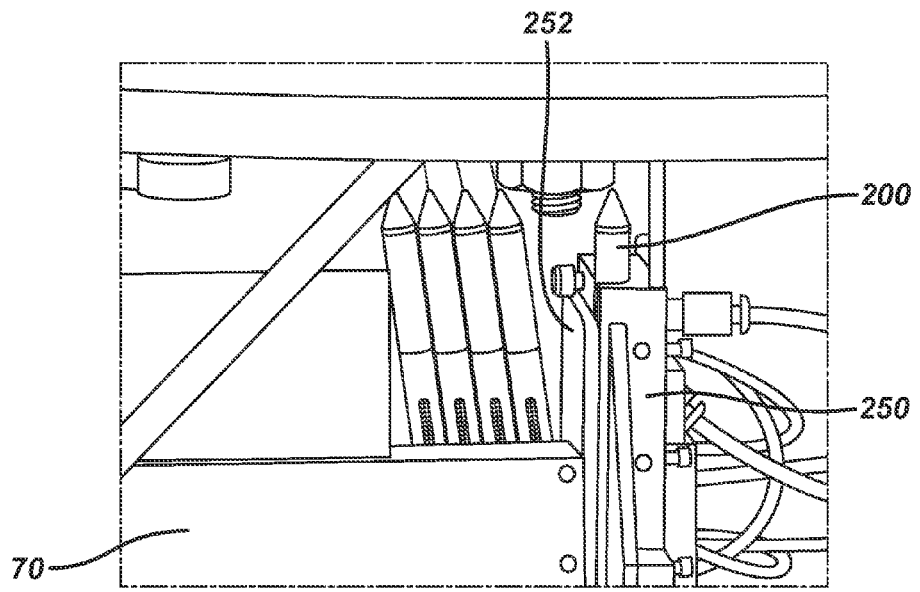

Referring to FIG. 20A, in one embodiment, the cartridge insertion rod 74 is retracted below the braider plate 58 for removing the empty cartridge from the enclosed area of the braider system. As the cartridge insertion rod 74 is retracted, the retractable gate 252 covering the cartridge chamber 250 preferably remains closed. FIG. 20B shows the braider system with the cartridge insertion rod retracted so that the empty cartridge 200 has been returned to the cartridge chamber 250. The retractable gate 252 remains closed for separating the empty cartridge 200 from the loaded cartridges positioned within the magazine 70.

Figure 20C:
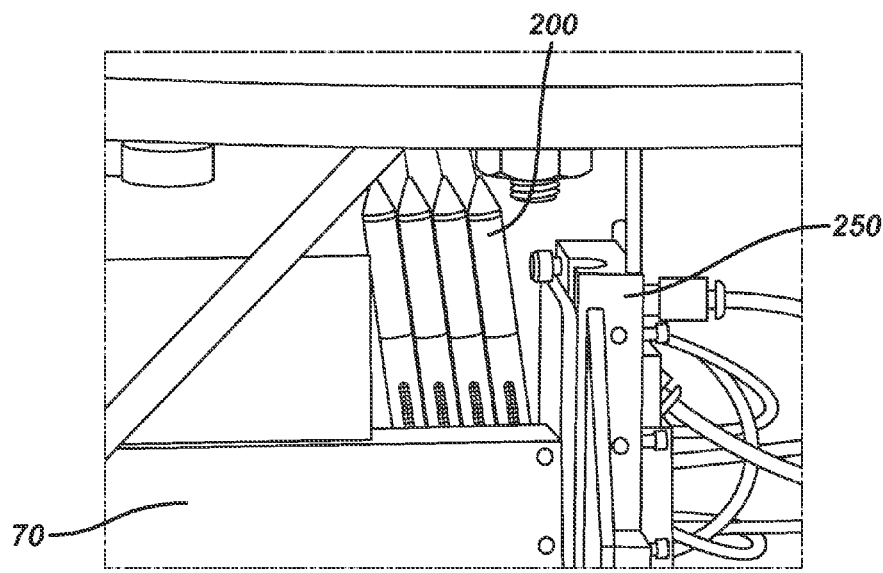
Figure 20D:
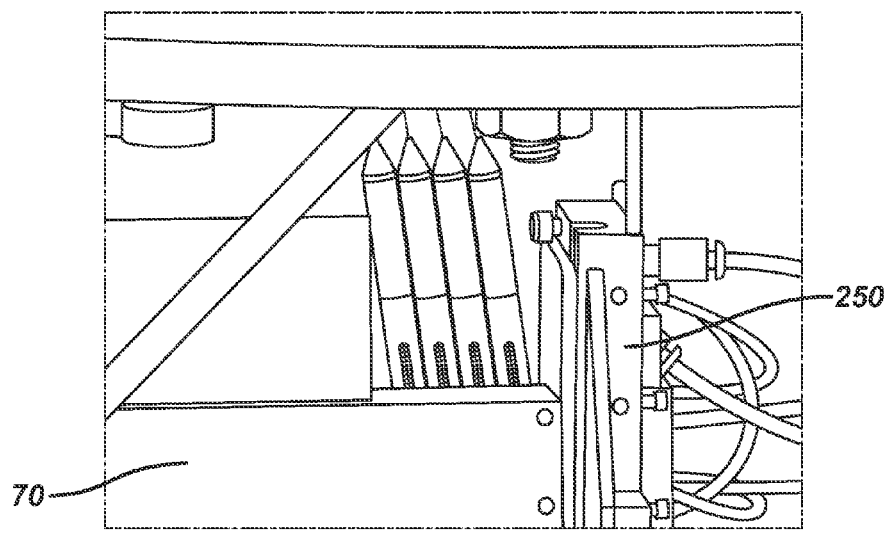

Referring to FIG. 20C, in one embodiment, the empty cartridge shown in FIG. 20B is preferably removed from the system through the cartridge ejection tube 78 shown in FIG. 1. Referring to FIG. 20D, after the empty cartridge has been removed through the cartridge ejection tube, the next lead cartridge 200 in the magazine 70 is prepared to be loaded into the cartridge chamber 250 to repeat the process described herein. This process is continuously repeated by the system controller to advance loaded cartridges into the filament winding apparatus for forming braided barbed sutures, and to remove empty cartridges from the system.

Figure 21:
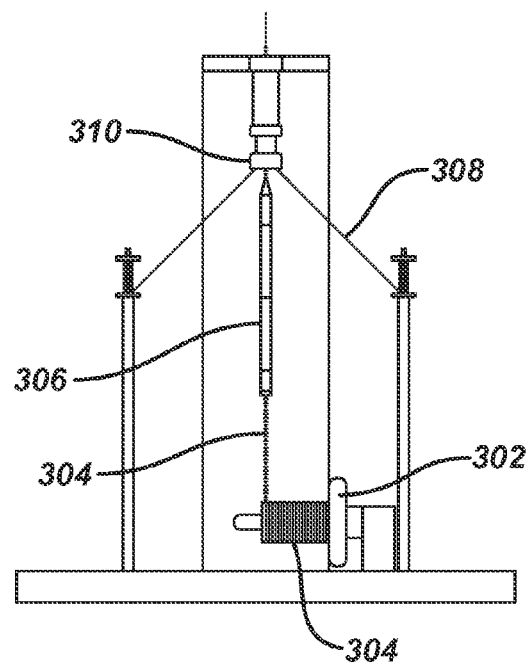
FIG. 21 shows an automated system for making braided barbed sutures, in accordance with one embodiment of the present invention.

Referring to FIG. 21, in one embodiment, an automated braiding system 300 includes a rotatable spool 302 having a continuous length of barbed insert material 304 provided thereon. The braider system 300 includes a guide 306 through which the barbed insert material 304 is passed. The guide 306 preferably has an opening or passageway, such as a slit opening, that is adapted to closely conform to the shape of the barbed suture material 304. The opening or passageway preferably enables the barbed insert material to move axially relative to the guide but prevents the barbed insert material 304 from rotating or twisting about its longitudinal axis relative to the guide 306. In one embodiment, the guide may be selectively rotatable for selectively rotating and/or twisting the continuous length of the barbed insert material 304 as the filaments 308 are wound about the barbed insert material. As noted above, in one embodiment, the barbed insert material 304 is preferably a continuous length of material that may be initially fed into the filament winding assembly to make braided barbed sutures. In one embodiment, if certain actions are not taken, an undesirable twist may build up in the continuous length of barbed insert material 304 before it reaches the guide 306. There are at least two ways to prevent this undesirable twist: 1) provide for a mechanism to rotate the entire spool of continuous barbed insert material in conjunction with any rotation of the guide 306 and/or 2) the guide 306 may rapidly reverse rotation to its start point once it reaches 180 degrees of rotation (for barbed inserts that have barbs oriented 180 degrees apart) or 360 degrees (for barbed inserts that have barbs on only one side), or other degrees of rotation based on the number of opposing barbs on the barbed insert (e.g., for equidistant barbs, the degrees of reverse rotation would be 360 divided by the number of equidistant barbs).

The automated system 300 shown in FIG. 21 preferably includes winding filaments 308 that are wrapped around the barbed insert material 304 at a braider eyelet 310. In one embodiment, as the barbed insert material 304 is advanced toward the braider eyelet 310, the guide 306 is preferably rotated about its longitudinal axis, which, in turn, rotates the barbed insert 304 about its longitudinal axis. As the rotatable guide 306 rotates the barbed insert material, the filaments 308 are helically wound about the barbed insert material 304 to form braided barbed sutures. In another embodiment, the guide may be locked in position so that it does not rotate around its longitudinal axis, which, in turn, will not rotate the barbed insert as it is introduced into the filament winding assembly.

Figure 22:
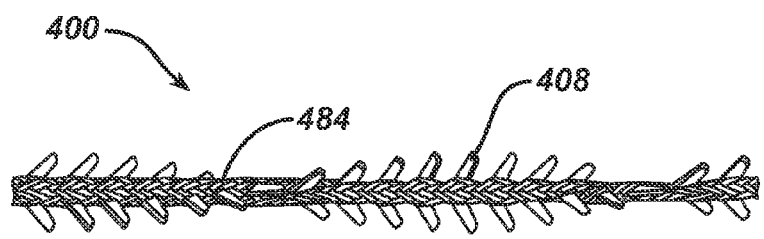
FIG. 22 shows a braided barbed suture having barbs projecting in multiple planes about a core, in accordance with one embodiment of the present invention.

FIG. 22 shows a braided barbed suture 400 that is formed using the system 300 shown in FIG. 21, whereby the guide 306 is rotated as the barbed insert is dispensed from the guide 306, which, in turn, rotates the barbed insert about its longitudinal axis as the filaments are wrapped around the barbed insert. The braided barbed suture 400 has filaments 484 helically wound about the core of the barbed insert. As a result of the helical winding, the barbs 408 are disposed in a 360° helical pattern. Although the present invention is not limited by any particular theory of operation, it is believed that providing barbs in a 360° pattern provides a braided barbed suture having greater holding strength.

In one embodiment, the barbed suture is made using a non-absorbable polymeric material, and a non-absorbable multi-filament polyester suture, commonly sold under the trademark Ethibond Excel by Ethicon, Inc., with surgical needles attached to both ends of the suture. A pledget, such as a Teflon pledget, may be positioned in the middle of the polymeric anchoring section.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A system for making braided barbed sutures comprising:
   a filament winding assembly;
   a barbed insert including an elongated core and barbs extending outwardly from said elongated core;
   a barbed insert dispenser opening defining a passageway for orienting said barbed insert as said barbed insert is dispensed into said filament winding assembly, wherein said barbed insert dispenser opening allows longitudinal movement of said barbed insert relative to said barbed insert dispenser opening while simultaneously preventing twisting movement of said barbed insert relative to said barbed insert dispenser opening.

2. The system as claimed in claim 1, further comprising a guide assembly including said barbed insert dispenser opening.

3. The system as claimed in claim 1, wherein said filament winding assembly comprises a plurality of filaments for winding around said barbed insert for making a braided barbed suture, wherein said filament winding assembly winds said filaments around said elongated core and between said barbs as said barbed insert is dispensed from said barbed insert dispenser opening.

4. The system as claimed in claim 1, wherein said passageway of said barbed insert dispenser opening allows longitudinal movement of said barbed insert relative to said passageway while simultaneously preventing twisting movement of said barbed insert relative to said passageway.

5. The system as claimed in claim 4, wherein said passageway has a size and a shape that substantially conforms to the size and shape of said barbed insert.

6. The system as claimed in claim 1, wherein said barbed insert comprises:
   said elongated core having a leading end, a trailing end, and a longitudinal axis extending between said leading and trailing ends thereof;
   a first set of said barbs extending outwardly from said elongated core; and
   a second set of said barbs extending outwardly from said elongated core and away from said first set of said barbs.

7. The system as claimed in claim 6, wherein said barbed insert further comprises a stopper located between said first and second sets of barbs.

8. The system as claimed in claim 1, wherein said barbed insert dispenser opening controls rotation of said barbed insert relative to said barbed insert dispenser opening when said barbed insert is in contact with said barbed insert dispenser opening.

9. The system as claimed in claim 2, further comprising a system controller having a central processing unit for controlling operation of said filament winding assembly and said guide assembly.

10. The system as claimed in claim 9, wherein said system controller has a first state in which said barbed insert dispenser opening is stationary as said barbed insert is dispensed into said filament winding assembly and a second state in which said barbed insert dispenser opening rotates as said barbed insert is dispensed into said filament winding assembly.

11. The system as claimed in claim 2, wherein said guide assembly comprises a cartridge including said barbed insert dispenser opening.

12. The system as claimed in claim 11, wherein said barbed insert is loaded into said cartridge so that a leading end of said barbed insert projects from said barbed insert dispenser opening.

13. The system as claimed in claim 12, wherein said guide assembly further comprises a magazine for holding a plurality of cartridges, said system further comprising a system controller having a subroutine for introducing said cartridges one at a time into said filament winding assembly.

14. The system as claimed in claim 13, wherein each said cartridge comprises an optical window for providing visual access to said barbed inserts loaded therein, and wherein said system controller further comprises an optical sensor for determining whether said barbed inserts are present in said cartridges.

15. The system as claimed in claim 14, wherein each said cartridge includes an outer surface, and wherein said guide assembly further comprises a cartridge insertion rod that engages the outer surfaces for affecting movement of said cartridges.

16. The system as claimed in claim 1, wherein said barbed suture dispenser opening comprises an elongated slit having a greater width than height.

17. The system as claimed in claim 16, wherein the greater width accommodates said barbs of said barbed insert.

18. A system for making braided barbed sutures comprising:
   a filament winding assembly including a plurality of filaments;
   a barbed insert including an elongated core and barbs extending outwardly from said elongated core;
   a cartridge for guiding said barbed insert toward said filament winding assembly, wherein said cartridge has a barbed insert dispenser opening adapted to enable longitudinal movement of said barbed insert through said barbed insert dispenser opening while simultaneously preventing twisting movement of said at least one barbed insert relative to said barbed insert dispenser opening;
   wherein said filament winding assembly winds said filaments around said elongated core and between said barbs as said barbed insert is dispensed from said barbed insert dispenser opening of said cartridge.

19. The system as claimed in claim 18, further comprising a braider eyelet for directing said plurality of filaments toward a braiding zone, and wherein said barbed insert dispenser opening is adapted to direct a leading end of said barbed insert into said braiding zone for winding said plurality of filaments around said barbed insert for making a braided barbed suture.

20. The system as claimed in claim 18, wherein said barbed insert dispenser opening has a size and a shape that substantially conforms to the size and shape of said barbed insert.

* * * * *